(12) United States Patent
Charles et al.

(10) Patent No.: US 8,765,432 B2
(45) Date of Patent: Jul. 1, 2014

(54) TARGETED DRUG PHOSPHORYLCHOLINE POLYMER CONJUGATES

(75) Inventors: Stephen A. Charles, San Jose, CA (US); D. Victor Perlroth, Palo Alto, CA (US)

(73) Assignee: Oligasis, LLC, Palo Alto, CA (US)

( * ) Notice: Subject to any disclaimer, the term of this patent is extended or adjusted under 35 U.S.C. 154(b) by 0 days.

(21) Appl. No.: 13/515,913

(22) PCT Filed: May 10, 2010

(86) PCT No.: PCT/US2010/034252
§ 371 (c)(1),
(2), (4) Date: Aug. 27, 2012

(87) PCT Pub. No.: WO2011/075185
PCT Pub. Date: Jun. 23, 2011

(65) Prior Publication Data
US 2013/0034517 A1    Feb. 7, 2013

Related U.S. Application Data

(60) Provisional application No. 61/288,127, filed on Dec. 18, 2009.

(51) Int. Cl.
```
A61P 35/00     (2006.01)
C07D 491/22    (2006.01)
C07D 491/147   (2006.01)
C12N 9/96      (2006.01)
A61K 47/48     (2006.01)
A61K 31/41     (2006.01)
```

(52) U.S. Cl.
CPC . *C12N 9/96* (2013.01); *A61K 31/41* (2013.01); *A61K 47/48169* (2013.01)
USPC ............... 435/188; 514/283; 546/48; 546/51

(58) Field of Classification Search
None
See application file for complete search history.

(56) References Cited

U.S. PATENT DOCUMENTS

| | | | |
|---|---|---|---|
| 5,741,923 A | 4/1998 | Driver et al. | |
| 5,763,548 A | 6/1998 | Matyjaszewski et al. | |
| 5,789,487 A | 8/1998 | Matyjaszewski et al. | |
| 5,807,937 A | 9/1998 | Matyjaszewski et al. | |
| 5,945,491 A | 8/1999 | Matyjaszewski et al. | |
| 6,111,022 A | 8/2000 | Matyjaszewski et al. | |
| 6,121,371 A | 9/2000 | Matyjaszewski et al. | |
| 6,124,411 A | 9/2000 | Matyjaszewski et al. | |
| 6,162,882 A | 12/2000 | Matyjaszewski et al. | |
| 6,407,187 B1 | 6/2002 | Matyjaszewski et al. | |
| 6,512,060 B1 | 1/2003 | Matyjaszewski et al. | |
| 6,538,091 B1 | 3/2003 | Matyjaszewski et al. | |
| 6,541,580 B1 | 4/2003 | Matyjaszewski et al. | |
| 6,555,593 B1 | 4/2003 | Hoyle et al. | |
| 6,583,272 B1 | 6/2003 | Bailon | |
| 6,624,262 B2 | 9/2003 | Matyjaszewski et al. | |
| 6,627,314 B2 | 9/2003 | Matyjaszewski et al. | |
| 6,759,491 B2 | 7/2004 | Matyjaszewski et al. | |
| 6,790,919 B2 | 9/2004 | Matyjaszewski et al. | |
| 6,852,816 B2 | 2/2005 | Lewis et al. | |
| 6,887,962 B2 | 5/2005 | Matyjaszewski et al. | |
| 7,019,082 B2 | 3/2006 | Matyjaszewski et al. | |
| 7,049,373 B2 | 5/2006 | Matyjaszewski et al. | |
| 7,056,455 B2 | 6/2006 | Matyjaszewski et al. | |
| 7,064,166 B2 | 6/2006 | Matyjaszewski et al. | |
| 7,125,938 B2 | 10/2006 | Matyjaszewski et al. | |
| 7,157,530 B2 | 1/2007 | Matyjaszewski et al. | |
| 7,300,990 B2 | 11/2007 | Lewis et al. | |
| 7,348,424 B2 | 3/2008 | Miyazawa et al. | |
| 7,569,655 B2 | 8/2009 | Pacetti et al. | |
| 2003/0143596 A1 | 7/2003 | Bentley et al. | |
| 2004/0063881 A1 | 4/2004 | Lewis et al. | |
| 2004/0253596 A1 | 12/2004 | Pawlak et al. | |
| 2005/0112088 A1 | 5/2005 | Zhao et al. | |
| 2005/0123501 A1 | 6/2005 | Lewis | |
| 2005/0159556 A1 | 7/2005 | Lewis et al. | |
| 2005/0180945 A1 | 8/2005 | Chaikof et al. | |
| 2006/0135714 A1 | 6/2006 | Lewis et al. | |
| 2006/0165804 A1 | 7/2006 | Lewis et al. | |
| 2006/0217285 A1 | 9/2006 | Destarac | |
| 2007/0141104 A1 | 6/2007 | Hauenstein | |
| 2008/0124450 A1 | 5/2008 | Pacetti | |
| 2008/0147178 A1 | 6/2008 | Pacetti et al. | |
| 2010/0158850 A1 | 6/2010 | Baker, Jr. et al. | |

FOREIGN PATENT DOCUMENTS

| | | |
|---|---|---|
| EP | 1465933 B1 | 8/2007 |
| EP | 1592719 B1 | 3/2008 |
| EP | 1732621 B1 | 12/2009 |
| EP | 2260873 A1 | 12/2010 |
| JP | 2010-117189 A | 5/2010 |
| WO | WO 00/59968 A1 | 10/2000 |
| WO | WO 02/28929 A1 | 4/2002 |
| WO | WO 03/062290 A1 | 7/2003 |
| WO | WO 03/074026 A1 | 9/2003 |

(Continued)

OTHER PUBLICATIONS

Venditto, et al. (Cancer Therapies Utilizing the Camptothecins: A Review of the in Vivo Literature, 7 Molecular Pharm. 307-49 (2010).*
Chen, et al., Polymeric phosphorylcholine-camptothecin conjugates prepared by controlled free radical polymerization and click chemistry, 20 Bioconjugate Chem. 2331-41 (2009).*
Lewis, et al., Poly(2-methacryloyloxyethyl phosphorylcholine) for protein conjugation, 19 Bioconjugate Chem. 2144-55 (2008).*
Bontempo, et al., "Cysteine-Reactive Polymers Synthesized by Atom Transfer Radical Polymerization for Conjugation to Proteins," *J. Am. Chem. Soc.*, (2004), 126, pp. 15372-15373.
Chen, et al., "Lubrication at Physiological Pressures by Polyzwitterionic Brushes," *Science*, (2009), 323, pp. 1698-1701.

(Continued)

*Primary Examiner* — H. Sarah Park
(74) *Attorney, Agent, or Firm* — Alston & Bird LLP

(57) ABSTRACT

The present invention provides random copolymers containing phosphorylcholine and one or more functional agents, and methods of preparing such random copolymers.

2 Claims, 1 Drawing Sheet

(56) References Cited

FOREIGN PATENT DOCUMENTS

| WO | WO 03/074090 A1 | 9/2003 |
|---|---|---|
| WO | WO 2004/063237 A1 | 7/2004 |
| WO | WO 2004/113394 A2 | 12/2004 |
| WO | WO 2005/028539 A2 | 3/2005 |
| WO | WO 2005/058367 A2 | 6/2005 |
| WO | WO 2007/005253 A1 | 1/2007 |
| WO | WO 2007/075534 A2 | 7/2007 |
| WO | 2007/100902 A2 | 9/2007 |
| WO | WO 2008/098930 A1 | 8/2008 |
| WO | WO 2008/112257 A1 | 9/2008 |
| WO | WO 2008/112289 A2 | 9/2008 |
| WO | WO 2010/068862 A2 | 6/2010 |
| WO | WO 2010/068864 A2 | 6/2010 |
| WO | WO 2010068864 A2 * | 6/2010 |
| WO | WO 2011/075185 A1 | 6/2011 |
| WO | WO 2011/075736 A2 | 6/2011 |
| WO | WO 2011/130694 A2 | 10/2011 |
| WO | WO 2013/059137 A1 | 4/2013 |

OTHER PUBLICATIONS

Chen, et al., "Polymeric Phosphorylcholine-Camptothecin Conjugates Prepared by Controlled Free Radical Polymerization and Click Chemistry," *Bioconjugate Chem.*, (2009), 20:12, pp. 2331-2341.
Crowe, et al., "Recombinant human respiratory syncytial virus (RSV) monoclonal antibody Fab is effective therapeutically when introduced directly into the lungs of RSV-infected mice," *Proc. Natl. Acad. Sci. USA*, (1994) 91 pp. 1386-1390.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," *Bioconjugate Chem.*, (2010), 21:1, pp. 169-174.
Dong, et al., "ARGET ATRP of 2-(Dimethylamino)ethyl Methacrylate as an Intrinsic Reducing Agent," *Macromolecules*, (2008), 41:19, pp. 6868-6870.
Dong, et al., "Well-Defined High-Molecular-Weight Polyacrylonitrile via Activators Regenerated by Electron Transfer ATRP," *Macromolecules*, (2007), 40:9, pp. 2974-2977.
Haddleton, et al., "Phenolic Ester-Based Initiators for Transition Metal Mediated Living Polymerization," *Macromolecules*, (1999), 32, pp. 8732-8739.
Heise, et al., "Investigation of the Initiation Behavior of a Dendritic 12-Arm Initiator in Atom Transfer Radical Polymerization," *Macromolecules*, (2001), 34:11, pp. 3798-3801.
Heredia, et al., "In Situ Preparation of Protein-'Smart' Polymer Conjugates with Retention of Bioactivity," *J. Am. Chem. Soc.*, (2005), 127, pp. 16955-16960.
Hong, et al., "Preparation of Segmented Copolymers in the Presence of an Immobilized/Soluble Hybride ATRP Catalyst Systems," *Macromolecules*, (2003), 36:1, pp. 27-35.
Iwasaki, et al., "Platelet compatible blood filtration fabrics using a phosphorylcholine polmer having high surface mobility," *Biomaterials*, (2003), 24, pp. 3599-3604.
Jakubowski, et al., "Activators Regenerated by Electron Transfer for Atom Transfer Radical Polymerization of Styrene," *Macromolecules*, (2006), 39:1, pp. 39-45.
Kizhakkedathu, et al., "Synthesis of Well-Defined Environmentally Responsive Polymer Brushes by Aqueous ATRP," *Macromolecules*, (2004), 37:3, pp. 734-743.
Kwiatdowski, et al., "High Molecular Weight Polymethacrylates by AGET ATRP under High Pressure," *Macromolecules*, (2008), 41:4, pp. 1067-1069.
Lacciardi, et al., "Synthesis of Novel Folic Acid-Functionalized Biocompatible Block Copolymers by Atom Transfer Radical Polymerization for Gene Delivery and Encapsulation of Hydrophobic Drugs," *Biomacromolecules*, (2005), 6:2, pp. 1085-1096.

Lena, et al., "Investigation of metal ligand affinities of atom transfer radical polymerization catalysts with a quadrupole ion trap," *Dalton Transactions*, (2009), 41, pp. 8884-8889.
Lewis, et al., "Crosslinkable coatings from phosphorylcholine-based polymers," *Biomaterials*, (2001), 22, pp. 99-111.
Lewis, et al., "Poly(2-methacryloyloxyethyl phosphorylcholine) for Protein Conjugation," *Bioconjugate Chem.*, (2008), 19:11, pp. 2144-2155.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," *Macromolecules*, (2006), 39:2, pp. 893-896.
Ma, et al., "Synthesis of Biocompatible Polymers. 1. Homopolymerization of 2-Methacryloyloxyethyl Phosphorylcholine via ATRP in Protic Solvents: An Optimization Study," *Macromolecules*, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," *Macromolecules*, (2003), 36:10, pp. 3475-3484.
Mantovani, et al., "Design and Synthesis of N-Maleimido-Functionalized Hydrophilic Polymers via Copper-Mediated Living Radical Polymerization: A Suitable Alternative to PEGylation," *J. Am. Chem. Soc.*, (2005), 127, pp. 2966-2973.
Matyjaszewski, et al., "Diminishing catalyst concentration in atom transfer radical polymerization with reducing agents," *PNAS*, (Oct. 17, 2006), 103:42, pp. 15309-15314.
Min, et al., "Use of Ascorbic Acid as Reducing Agent for Synthesis of Well-Defined Polymers by ARGET ATRP," *Macromolecules*, (2007), 40:6, pp. 1789-1791.
Miyamoto, et al., "Effect of water-soluble phospholipid polymers conjugated with papain on the enzymatic stability," *Biomaterials*, (2004), 25, pp. 71-76.
Ng, et al., "Successful Cu-Mediated Atom Transfer Radical Polymerization in the Absence of Conventional Chelating Nitrogen Ligands," *Macromolecules*, (2010), 43:2, pp. 592-594.
Oh, et al., "Preparation of Poly(oligo(ethylene glycol) monomethyl ether methacrylate) by Homogeneous Aqueous AGET ATRP," *Macromolecules*, (2006), 39:9, pp. 3161-3167.
PCT/US2007/005372 International Search Report and Written Opinion mailed Aug. 8, 2008.
PCT/US2010/034252 International Search Report and Written Opinion mailed Sep. 9, 2010.
PCT/US2010/61358 International Search Report and Written Opinion mailed May 9, 2011.
PCT/US2010/32768 International Search Report and Written Opinion mailed Dec. 16, 2011.
PCT/US2012/60301 International Search Report and Written Opinion mailed Feb. 27, 2013.
Pietrasik, et al., "Synthesis of High Molecular Weight Poly(styrene-co-acrylonitrile) Copolymers with Controlled Architecture," *Macromolecules*, (2006), 39:19, pp. 6384-6390.
Ranganathan, et al., "Synthesis of Thermoresponsive Mixed Arm Star Polymers by Combination of RAFT and ATRP from a Multifunctional Core and Its Self-Assembly in Water," *Macromolecules*, (2008), 41:12, pp. 4226-4234.
Roberts, et al., "Chemistry for peptide and protein PEGylation," *Advanced Drug Delivery Reviews*, (2002), 54, pp. 459-476.
Ruiz, et al., "Synthesis structure and surface dynamics of phosphorylcholine functional biomimicking polymers," *Biomaterials*, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," *Journal of Controlled Release*, (2009), 135, pp. 51-59.
Sakaki, et al., "Stabilization of an antibody conjugated with enzyme by 2-methacryloyloxyethyl phosphorylcholine copolymer in enzyme-linked immunosorbent assay," *J Biomed Mater Res*, (1999), 47, pp. 523-528.
Samanta, et al., "End-Functionalized Phosphorylcholine Methacrylates and their Use in Protein Conjugation," *Biomacromolecules*, (2008), 9:(10), pp. 2891-2897.

(56) References Cited

OTHER PUBLICATIONS

Sayers, et al., "The Reduced Viscosity of PolyPEG® Compared with Linear PEG," Poster, Warwick Effect Polymers Ltd, retrieved from <http:www.wep-ltd.co.uk> on Feb. 11, 2009.
Tao, et al., "α-Aldehyde Terminally Functional Methacrylic Polmers from Living Radical Polymerization: Application in Protein Conjugation 'Pegylation'," *J. Am. Chen. Soc.*, (2004), 126:41, pp. 13220-13221.
U.S. Appl. No. 12/281,071, Office Action mailed Feb. 7, 2012.
U.S. Appl. No. 12/281,071, Restriction Requirement notified Jun. 20, 2011.
U.S. Appl. No. 13/515,913, Restricton Requirement mailed Aug. 14, 2013.
U.S. Appl. No. 13/516,173, Restriction Requirement mailed Sep. 3, 2013.
U.S. Appl. No. 13/959,563, Office Action mailed Oct. 10, 2013.
Wang, et al., "Controlled/'Living' Radical Polymerization. Atom Transfer Radical Polymerization in the Presence of Transition-Metal Complexes," *J. Am. Chem. Soc.*, (1995), 117:20, pp. 5614-5615.
Warwick Effect Polymers, PowerPoint presentation, "Polymers for the Healthcare and Speciality Materials Industries," Jan. 2009, pp. 1-29.
Yaseen, et al., "The Structure of Zwitterionic Phosphocholine Surfactant Monolayers," *Langmuir*, (2006), 22:13, pp. 5825-5832.
International Search Report from PCT/US2010/034252, Sep. 9, 2010.

\* cited by examiner

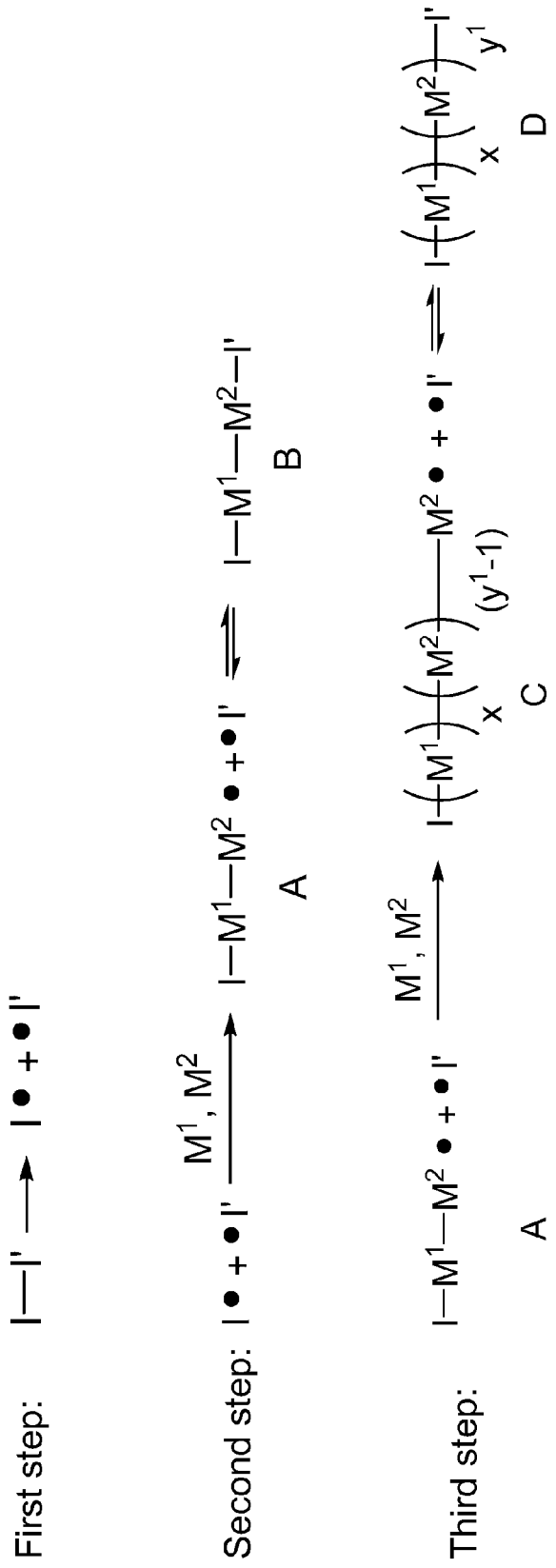

TARGETED DRUG PHOSPHORYLCHOLINE POLYMER CONJUGATES

CROSS-REFERENCES TO RELATED APPLICATIONS

This application is the U.S. National Stage entry of PCT/US2010/034252, filed May 10, 2010, which claims priority to U.S. Provisional Application No. 61/288,127, filed Dec. 18, 2009; each of which is herein incorporated by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

An arms race of sorts is happening right now amongst the pharmaceutical companies who are all trying to deliver 'medically differentiated products'. Current drug formats are inflexible, in that they generally allow for a single activity. For example, a recombinant monoclonal antibody generally is designed and optimized to bind and inhibit a single target protein. For example, a small molecule drug is generally designed and optimized to bind and activate (or inhibit) a single target. In some cases, the drug is not selective and there are multiple activities (for example, a small molecule kinase inhibitor that is designed to bind the ATP binding site of a single kinase but which shows a level of affinity and bioactivity against adjacent kinase family members). But generally drug developers optimize using today's drug formats for single activities and non-selectivity is seen as something to engineer away in the drug development process.

In today's drug development, then, the selection of the single target is the key variable. Drugs, therefore, are developed from a format-centric point of view. But drugs are developed to treat disease. And diseases generally are composed of more than one pathophysiologic mechanism happening in series or in parallel. A mechanism being a pathway or set of intersecting pathways occurring either in a localized cell or tissue or organ or systemically throughout the organism. A pathway being a set of moieties that interact with each other. A more ideal way to engage in drug development is to be able to take a disease-centric or biology-centric approach. For example, based on the sum of academic and corporate and historical research and experience to date, disease x involves pathways a, b, and c. Within pathway a, target protein z is known to be upregulated (and could be bound and inhibited by an antibody fragment). Within pathway b, cell-type y is known to be proliferating inappropriately (and could be impacted by a small molecule anti-proliferative agent). And the pathophysiology of pathway a and b is occurring within tissue subtype x (and which could be targeted or enriched with drug by including on the drug several copies of a small tissue-targeting peptide). It would be ideal to have a drug technology or format that allowed these multiple functions and different types of bioactive moieties (protein, oligonucleotide, small molecule, lipid, etc.) to be integrated into a single, adaptable, multi-functional drug that is a practical best-of-breed and straightforward in its design, implementation, manufacturing, and administration. In addition, the technology should allow for certain of the bioactive moieties to be unstably attached such that they can be released under the desired conditions (time, aqueous pH environment, other). These drugs should demonstrate higher efficacy and safety while providing a higher overall probability of technical, regulatory, and commercial success from early in the drug development process.

Most diseases are complex and multifactorial in origin. Therefore, in applying this biology-centric or disease-centric approach, one could imagine a future ten or fifteen years down the road where a big disease such as rheumatoid arthritis is actually divided through diagnostic (molecular, imaging, biomarker, genetic) or other approaches into, say, ten major subtypes each of which is driven by a particular set of pathophysiologies and which can be targeted using one multi-functional drug such that ten multi-functional drugs are developed in order to treat the ten different disease types.

The present invention describes such a drug technology format that can be the backbone of the next-generation of multi-functional drug development. The technology delivers a polymer backbone which (i) itself delivers fundamental biocompatibility to the drug through the selection of hydrophilic monomer and architecture, and (ii) also forms a core backbone for conjugation and/or adsorption to multiple agents of different types (amino acid, small molecule, oligonucleotide, lipid, other, diagnostic agent, imaging agent, therapy monitoring agent), predefined stoichiometries and functions (biocompatibility, spacer, bioactivity, targeting, diagnostic, imaging, other), and (iii) can employ any stable or flexible (under predefined conditions) conjugation chemistry.

Hydrophilic polymers for drug conjugation have been well described and the drug conjugates are generating in excess of $5 billion revenue per annum. What is important for these polymers is the extent to which they bind water molecules and the physical properties of those water binding interactions. This combination of properties drives the fundamental biocompatibility of the polymer. PEG is one example of a hydrophilic polymer, but there are other examples of hydrophilic polymers that bind water to a different extent and with different physical properties and therefore with different fundamental biocompatibility. One such example is phosphorylcholine-based polymers, specifically polymers derived from 2-methacryloyloxyethyl phosphorylcholine, which polymers have been commercialized in various forms in medical devices such as coronary drug eluting stents and contact lenses. In recent years, new methods of controlled radical polymerization have been developed with the promise to enable the manufacture of large, complex-architecture polymers with low cost and high quality.

The present invention integrates a drug technology and format that allows for a new paradigm of drug development, starting with a set of biologies driving disease pathophysiology; integrating biocompatibility moieties, drug moieties of different classes, extended architectures, flexible chemistries, all in a practical package. More simply put, the present invention presents a drug format that allows the user to create a nanoscale biomachine with the goal of creating magic bullets for combating diseases to the benefit of patients.

Efforts to formulate biologically active agents for delivery must deal with a variety of variables including the route of administration, the biological stability of the active agent and the solubility of the active agents in physiologically compatible media. Choices made in formulating biologically active agents and the selected routes of administration can affect the bioavailability of the active agents. For example, the choice of parenteral administration into the systemic circulation for biologically active proteins and polypeptides avoids the proteolytic environment found in the gastrointestinal tract. However, even where direct administration, such as by injection, of biologically active agents is possible, formulations may be unsatisfactory for a variety of reasons including the generation of an immune response to the administered agent and responses to any excipients including burning and stinging. Even if the active agent is not immunogenic and satisfactory excipients can be employed, biologically active agents can have a limited solubility and short biological half-life that can require repeated administration or continuous infusion, which can be painful and/or inconvenient.

For some biologically active agents a degree of success has been achieved in developing suitable formulations of functional agents by conjugating the agents to water soluble polymers. The conjugation of biologically active agents to water soluble polymers is generally viewed as providing a variety of benefits for the delivery of biologically active agents, and in particular, proteins and peptides. Among the water soluble polymers employed, polyethylene glycol (PEG) has been most widely conjugated to a variety of biologically active agents including biologically active peptides. A reduction in immunogenicity or antigenicity, increased half-life, increased solubility, decreased clearance by the kidney and decreased enzymatic degradation have been attributed to conjugates of a variety of water soluble polymers and functional agents, including PEG conjugates. As a result of these attributes, the polymer conjugates of biologically active agents require less frequent dosing and may permit the use of less of the active agent to achieve a therapeutic endpoint. Less frequent dosing reduces the overall number of injections, which can be painful and which require inconvenient visits to healthcare professionals. Conjugation of PEG or other polymers can also modify the core activity of the drug itself—the idea of "additional bioactivities conferred to the drug by virtue of polymer conjugation (for example, the large hydrodynamic radius broadens the scope of inhibition from drug (antibody fragment) inhibits binding to receptor A but polymer-drug conjugate inhibits binding to receptor A plus receptor B as a function of any number of different mechanisms but certainly steric hindrance.

Although some success has been achieved with PEG conjugation, "PEGylation" of biologically active agents remains a challenge. As drug developers progress beyond very potent agonistic proteins such as erythropoietin and the various interferons, the benefits of the PEG hydrophilic polymer are insufficient to drive the increases in solubility, stability and the decreases in viscosity and immunogenicity that are necessary for a commercially successful product that is subcutaneously administered. PEG conjugation may also result in the loss of biological activity. A variety of theories have been advanced to account for loss of biological activity upon conjugation with PEG. These include blockage of necessary sites for the agent to interact with other biological components, either by the conjugation linkage or by the agent being buried within the PEG conjugate, particularly where the polymer is long and may "wrap" itself around some of the active agent, thereby blocking access to potential ligands required for activity.

Branched forms of PEG for use in conjugate preparation have been introduced to alleviate some of the difficulties encountered with the use of long straight PEG polymer chains. While branched polymers may overcome some of the problems associated with conjugates formed with long linear PEG polymers, neither branched nor linear PEG polymer conjugates completely resolve the issues associated with the use of conjugated functional agents. Both linear and branched PEG conjugates can, for example, suffer from rates of degradation that are either too long or too short. A rapid rate of degradation can result in a conjugate having too short of an in vivo half-life, whereas, too slow of a rate of degradation can result in an unacceptably long conjugate half-life in vivo.

In view of the recognized advantages of conjugating functional agents to water soluble polymers, and the limitations of water soluble polymers such as PEG in forming conjugates suitable for therapeutic purposes, additional water soluble polymers for forming conjugates with functional agents are desirable. Water soluble polymers, particularly those which have many of the advantages of PEG for use in conjugate formation, and which do not suffer from the disadvantages observed with PEG as a conjugating agent would be desirable for use in forming therapeutic and diagnostic agents. To this end, polymers of 2-methacryloyloxyethyl-phosphorylcholine are set forth for use in preparing conjugates of biologically active agents.

BRIEF SUMMARY OF THE INVENTION

In one embodiment, the random copolymers of the present invention have formula I:

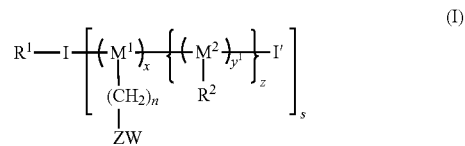

Each monomer $M^1$ and $M^2$ of formula I can independently be an acrylate, methacrylate, acrylamide, methacrylamide, styrene, vinyl-pyridine or a vinyl-pyrrolidone. Moreover, $R^1$ of formula I can independently be H, $L^1$-$A^1$, a linking group $LG^1$ or $L^1$-$LG^1$, and each $R^2$ of formula I is independently H, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, $L^2$-$LG^2$, $I^2$ and $L^2$-$I^2$. The group ZW of formula I is a zwitterionic moiety. The groups I and I' of formula I can each independently be an initiator fragment, such that the combination of I-I' is an initiator, $I^1$, for the polymerization of the random copolymer of formula I. Alternatively, I' can be H or $C_{1-6}$ alkyl. The group $I^2$ is an initiator. In addition, each of the groups $L^1$ and $L^2$ is a linker, each of the groups $A^1$ and $A^2$ is a functional agent, and each of the groups $LG^1$ and $LG^2$ is a linking group. In formula I above, subscripts x and $y^1$ are each independently an integer of from 1 to 1000, subscript z is an integer of from 1 to 10, subscript s is an integer of from 1 to 100, and subscript n is an integer of from 1 to 20, wherein either $R^1$ is $L^1$-$A^1$ or one of $R^2$ is $L^2$-$A^2$.

In other embodiments, the present invention provides a process for preparing a random copolymer of the present invention, the process including the step of contacting a mixture of a first monomer and a second monomer with an initiator, $I^1$, under conditions sufficient to prepare a random copolymer via free radical polymerization, wherein the first monomer comprises a phosphorylcholine, and each of the second monomer and initiator independently comprise at least one of a functional agent or a linking group for linking to the functional agent.

In another embodiment, the random copolymers of the present invention have a first monomer with phosphorylcholine, at least one second monomer having a functional agent or a linking group, and an initiator moiety having a functional agent or a linking group, wherein the functional agent is linked to the second monomer or the initiator moiety via a linker.

In yet other embodiments, the present invention provides a method of treating cancer, by administering a therapeutically effective amount of the random copolymer of formula I to a subject in need thereof, thereby treating cancer.

BRIEF DESCRIPTION OF THE DRAWINGS

FIG. 1 shows a scheme for the preparation of the random copolymers of the present invention. In the first step, the initiator I-I' is cleaved into the initiator fragments I and I', where initiator fragment I' is stabilized by the presence of a metal and ligand. The initiator fragment I then reacts with comonomers $M^1$ and $M^2$ in the second step to begin the polymerization process. The radical originally present on the initiator fragment I is not present on the last monomer to react, in this case comonomer $M^2$ (species A). The initiator fragment I' can then react with species A to reversibly terminate the polymerization, forming species B. Alternatively, species A can react with additional monomers to continue growing the polymer (species C), as shown in the third step. Finally, the growing polymer chain of species C is terminated by the metal and ligand stabilized initiator fragment I' to form the random copolymer, species D.

DETAILED DESCRIPTION OF THE INVENTION

I. General

The present invention provides random copolymers having phosphorylcholine, and at least one functional agent (as defined herein). Phosphorylcholine as a highly biocompatible molecule drives fundamental biocompatibility. It also has chaperone type functions, in terms of protecting proteins under temperature or other stress. It also can allow other functions such as reversible cellular uptake. The functional agent can be a bioactive agent such as a drug, therapeutic protein or targeting agent, as well as a detection agent, imaging agent, labeling agent or diagnostic agent. The random copolymers are useful for the treatment of a variety of conditions and disease states by selecting one or more appropriate functional agents. Multiple bioactive agents can be linked to the random copolymer, thus enabling treatment of not just a single disease symptom or mechanism, but rather the whole disease. In addition, the random copolymers are useful for diagnostic and imaging purposes by attachment of suitable targeting agents and imaging agents. The random copolymers can include both therapeutic and diagnostic agents in a single polymer, providing theranostic agents that treat the disease as well as detect and diagnose.

The random polymers can be prepared via a conventional free-radical polymerization or controlled/living radical polymerization, such as atom transfer radical polymerization (ATRP), using monomers that contain the phosphorylcholine and monomers that contain one or more bioactive agents which may be the same or different, or linking groups that are able to link to the bioactive agents. The initiators used for preparation of the random copolymers can have multiple initiating sites such that multi-arm polymers, such as stars, can be prepared. The initiator can also contain either the bioactive agent, or linking groups that are able to link to the bioactive agent.

II. Definitions

For the purpose of the present invention the following terminology will be used in accordance with the definitions set forth below.

"Random copolymer" refers to a polymer having at least two different monomer groups that are distributed randomly throughout the polymer backbone. The monomers of the random copolymer are the chemical moieties that are bonded together to form the polymer. Each distinct chemical moiety is termed a monomer. The random copolymers are prepared from monomers that include, but are not limited to, acrylates, methacrylates, acrylamides, methacrylamides, styrenes, vinyl-pyridine and vinyl-pyrrolidone. Additional monomers are useful in the random copolymers of the present invention. When two different monomers are used, such as in the random copolymers of the present invention, the two monomers are called "comonomers," meaning that the different monomers are copolymerized to form a single polymer.

"Zwitterionic moiety" refers to a compound having both a positive and a negative charge. Zwitterionic moieties useful in the random copolymers can include a quaternary nitrogen and a negatively charged phosphate, such as phosphorylcholine: RO—P(=O)(O$^-$)—O—CH$_2$CH$_2$—N$^+$(Me)$_3$. Other zwitterionic moieties are useful in the random copolymers of the present invention.

"Initiator" refers to a compound capable of initiating a polymerization using the comonomers of the present invention. The polymerization can be a conventional free radical polymerization or a controlled/living radical polymerization, such as Atom Transfer Radical Polymerization (ATRP) or Reversible Addition-Fragmentation-Termination (RAFT) polymerization. The initiator contains a labile bond that is cleaved to form two initiator fragments. When the initiator is suitable for ATRP, the labile bond can homolytically cleave to form two initiator fragments, the first being a radical capable of initiating a radical polymerization, and the second being a radical stabilized by a metal ion and a ligand. The second radical, initiator fragment I', reacts with the radical of the growing polymer chain to reversibly terminate the polymerization. The second initiator fragment I' is typically a halogen.

"Linker" refers to a chemical moiety that links two groups together. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Nonlimiting examples include those illustrated in Table 1.

"Hydrolyzable linker" refers to a chemical linkage or bond, such as a covalent bond, that undergoes hydrolysis under physiological conditions. The tendency of a bond to hydrolyze may depend not only on the general type of linkage connecting two central atoms between which the bond is severed, but also on the substituents attached to these central atoms. Non-limiting examples of hydrolytically susceptible linkages include esters of carboxylic acids, phosphate esters, acetals, ketals, acyloxyalkyl ether, imines, orthoesters, and some amide linkages.

"Enzymatically cleavable linker" refers to a linkage that is subject to degradation by one or more enzymes. Some hydrolytically susceptible linkages may also be enzymatically degradable. For example esterases may act on esters of carboxylic acid or phosphate esters, and proteases may act on peptide bonds and some amide linkages.

"pH sensitive linker" refers to a linkage that is stable at one pH and subject to degradation at another pH. For example, the pH sensitive linker can be stable at neutral or basic conditions, but labile at mildly acidic conditions.

"Photolabile linker" refers to a linkage, such as a covalent bond, that cleaves upon exposure to light. The photolabile linker includes an aromatic moiety in order to absorb the incoming light, which then triggers a rearrangement of the bonds in order to cleave the two groups linked by the photolabile linker.

"Functional agent" is defined to include a bioactive agent or a diagnostic agent. A "bioactive agent" is defined to include any agent, drug, compound, or mixture thereof that targets a specific biological location (targeting agent) and/or provides some local or systemic physiological or pharmacologic effect that can be demonstrated in vivo or in vitro. Non-limiting examples include drugs, vaccines, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, etc). A "diagnostic agent" is defined to include any agent that enables the detection or imaging of a tissue or disease. Examples of diagnostic agents include, but are not limited to, radiolabels, fluorophores and dyes.

"Therapeutic protein" refers to peptides or proteins that include an amino acid sequence which in whole or in part makes up a drug and can be used in human or animal pharmaceutical applications. Numerous therapeutic proteins are known to practitioners of skill in the art including, without limitation, those disclosed herein.

"Phosphorylcholine," also denoted as "PC," refers to the following:

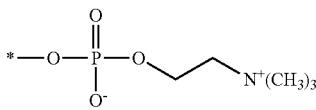

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. It is specifically contemplated that in each instance where a phosphorylcholine containing polymer is specified in this application for a particular use, a single phosphorylcholine can also be employed in such use.

"Poly(acryloyloxyethyl phosphorylcholine) containing polymer" refers to a polymer of acrylic acid containing at least one acryloyloxyethyl phosphorylcholine monomer such as 2-methacryloyloxyethyl phosphorylcholine (i.e., 2-methacryloyl-2'-trimethylammonium ethyl phosphate).

"Contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

"Water-soluble polymer" refers to a polymer that is soluble in water. A solution of a water-soluble polymer may transmit at least about 75%, more preferably at least about 95% of light, transmitted by the same solution after filtering. On a weight basis, a water-soluble polymer or segment thereof may be at least about 35%, at least about 50%, about 70%, about 85%, about 95% or 100% (by weight of dry polymer) soluble in water.

"Molecular weight" in the context of the polymer can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. The polymeric reagents of the invention are typically polydisperse (i.e., number average molecular weight and weight average molecular weight of the polymers are not equal), possessing low polydispersity values of preferably less than about 1.5, as judged by gel permeation chromatography. In other embodiments the polydispersities may be in the range of about 1.4 to about 1.2, more preferably less than about 1.15, still more preferably less than about 1.10, yet still more preferably less than about 1.05, and most preferably less than about 1.03.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

"About" as used herein means variation one might see in measurements taken among different instruments, samples, and sample preparations.

"Protected,", "protected form", "protecting group" and "protective group" refer to the presence of a group (i.e., the protecting group) that prevents or blocks reaction of a particular chemically reactive functional group in a molecule under certain reaction conditions. Protecting group will vary depending upon the type of chemically reactive group being protected as well as the reaction conditions to be employed and the presence of additional reactive or protecting groups in the molecule, if any. The skilled artisan will recognize protecting groups known in the art, such as those found in the treatise by Greene et al., "Protective Groups In Organic Synthesis," 3$^{rd}$ Edition, John Wiley and Sons, Inc., New York, 1999.

"Spacer," and "spacer group" are used interchangeably herein to refer to an atom or a collection of atoms optionally used to link interconnecting moieties such as a terminus of a water-soluble polymer and a reactive group of a functional agent and a reactive group. A spacer may be hydrolytically stable or may include a hydrolytically susceptible or enzymatically degradable linkage.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" in the context of this invention is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R'' and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

As used herein, the term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

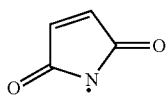

which upon reaction with a sulfhydryl (e.g., a thio alkyl) forms an —S-maleimido group having the structure

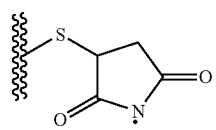

where "." indicates the point of attachment for the maleimido group and "⚡" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single monomer derived backbone.

"Branched," in reference to the geometry, architecture or overall structure of a polymer, refers to polymer having 2 or more polymer "arms" extending from a single group, such as an L group that may be derived from an initiator employed in an atom transfer radical polymerization reaction. A branched polymer may possess 2 polymer arms, 3 polymer arms, 4 polymer arms, 5 polymer arms, 6 polymer arms, 7 polymer arms, 8 polymer arms or more. For the purpose of this disclosure, compounds having three or more polymer arms extending from a single linear group are denoted as having a "comb" structure or "comb" architecture. Branched can also be achieved through "statistical" structures to create broader dendrimer-like architectures.

"Pharmaceutically acceptable" composition or "pharmaceutical composition" refers to a composition comprising a compound of the invention and a pharmaceutically acceptable excipient or pharmaceutically acceptable excipients.

"Pharmaceutically acceptable excipient" and "pharmaceutically acceptable carrier" refer to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose and the like.

"Patient" or "subject in need thereof" refers to a living organism suffering from or prone to a condition that can be prevented or treated by administration of a pharmaceutical composition as provided herein. Non-limiting examples include humans, other mammals and other non-mammalian animals.

"Therapeutically effective amount" refers to an amount of a conjugated functional agent or of a pharmaceutical composition useful for treating, ameliorating, or preventing an identified disease or condition, or for exhibiting a detectable therapeutic or inhibitory effect. The effect can be detected by any assay method known in the art.

The "biological half-life" of a substance is a pharmacokinetic parameter which specifies the time required for one half of the substance to be removed from an organism following introduction of the substance into the organism.

III. Phosphorylcholine-Containing Random Copolymers

The present invention provides random copolymers having zwitterionic groups, such as phosphorylcholine, and at least one functional agent. In some embodiments, the random copolymers of the present invention have a first monomer with phosphorylcholine, at least one second monomer having a functional agent or a linking group, and an initiator moiety having a functional agent or a linking group, wherein the functional agent can be linked to the second monomer or the initiator moiety via a linker.

In other embodiments, the random copolymers of the present invention have formula I:

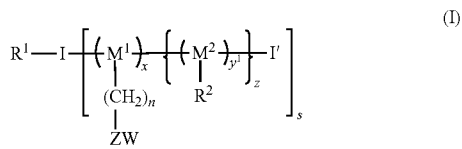

In formula I, the monomer units $M^1$ and $M^2$ are any monomers suitable for polymerization via controlled free radical methods, such as atom-transfer radical polymerization (ATRP). Each of monomers $M^1$ and $M^2$ can have any suitable number of comonomers in the random copolymer, as defined by radicals x and $y^1$, respectively. The $M^1$ monomer is linked to a zwitterionic group ZW, such as phosphorylcholine, via an alkylene chain (as defined by radical n). The random copolymers can include a single comonomer $M^2$ (radical z is 1), or can include several comonomers $M^2$ (z is greater than 1) wherein the different comonomers $M^2$ are the same or different. The comonomers $M^2$ are each linked to an $R^2$ group that can be inert but modifies the properties of the random copolymer (such as alkyl, aryl, etc.), or the $R^2$ groups can be functional such as when the $R^2$ group includes a functional agent A, a linking group LG or an initiator I. When the $R^2$ group includes one of these functional groups, the functional group can optionally be linked to the comonomer $M^2$ via a linker L. The $R^2$ groups can include a variety of functional groups and inert groups to tune the properties and functionality of the random copolymer. For example, several different targeting agents can be included along with several different drugs or therapeutic proteins as functional agents A. The monomers $M^1$ and $M^2$ can be polymerized by an initiator, $I^1$, that includes two initiator fragments I and I'. The initiator fragment I can be any group that initiates the polymerization. The initiator fragment I' can be any group that will reversibly terminate the growing polymer chain. The initiator fragment I' can be a halogen such as bromine, allowing the end of the polymer to be functionalized after polymerization. In addition, the initiator fragment I can be functionalized with an $R^1$ group that can include a variety of functional groups to tune the functionality of the random copolymer. For example, the $R^1$ group can include a functional agent A or a linking group LG, each optionally linked to initiator fragment I via a linker L. Moreover, the initiator fragment I can have multiple initiating sites such that the product polymer has several polymer arms (radical s greater than 1).

In some embodiments, each monomer $M^1$ and $M^2$ of formula I can independently be an acrylate, methacrylate, acrylamide, methacrylamide, styrene, vinyl-pyridine or a vinyl-pyrrolidone. Moreover, $R^1$ of formula I can independently be H, $L^1$-$A^1$, a linking group $LG^1$ or $L^1$-$LG^1$, and each $R^2$ of formula I is independently H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, $L^2$-$LG^2$, $I^2$ and $L^2$-$I^2$. The group ZW of formula I is a zwitterionic moiety. The groups I and I' of formula I can each independently be an initiator fragment, such that the combination of I-I' is an initiator, $I^1$, for the polymerization of the random copolymer of formula I. Alternatively, I' can be H or $C_{1-6}$ alkyl. The group $I^2$ is an initiator. In addition, each of the groups $L^1$ and $L^2$ is a linker, each of the groups $A^1$ and $A^2$ is a functional agent, and each of the groups $LG^1$ and $LG^2$ is a linking group. In formula I above, subscripts x and $y^1$ are each independently an integer of from 1 to 1000, subscript z is an integer of from 1 to 10, subscript s is an integer of from 1 to 100, and subscript n is an integer of from 1 to 20, wherein either $R^1$ is $L^1$-$A^1$ or one of $R^2$ is $L^2$-$A^2$.

The random copolymers of the present invention can have any suitable number of repeat units for each of the monomers $M^1$ and $M^2$. Exemplary ranges of repeat units for each comonomer include, but are not limited to, from about 1 to about 10,000, from about 10 to about 5,000, from about 10 to about 2,000, from about 10 to about 1,500, from about 10 to about 1,000, from about 100 to about 1,000, from about 100 to about 900, from about 100 to about 800, from about 100, to about 700, from about 100 to about 600, and from about 100 to about 500. When multiple $M^2$ monomers are present, each $M^2$ monomer can have a different number of repeat units.

The random copolymers of the present invention can have any suitable molecular weight. Exemplary molecular weights for the random copolymers of the present invention can be from about 1000 to about 200,000 Daltons (Da). In some embodiments, the random copolymers of the present invention can have a molecular weight of about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, about 75,000 Daltons, about 80,000 Daltons, about 90,000 Daltons, about 100,000 Daltons, about 120,000 Daltons, about 140,000 Daltons about 150,000 Daltons and about 175,000 Daltons.

The random copolymers of the present invention can also have any suitable number of comonomers, $M^2$. For example, the number of comonomers, subscript z, can be from 1 to 10, such as 1, 2, 3, 4, 5, 6, 7, 8, 9 or 10. The number of comonomers, subscript z, can also be from 1 to 5, 1 to 4, 1 to 3, or 1 to 2. In some embodiments, the random copolymer of the present invention can have two different monomers where subscript z is 1, such as in formula II:

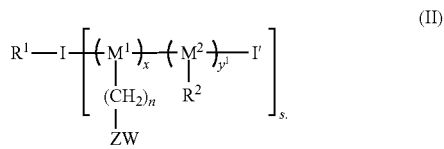

In other embodiments, the random copolymer can have 3 different monomers where subscript z is 2, such as in formula III:

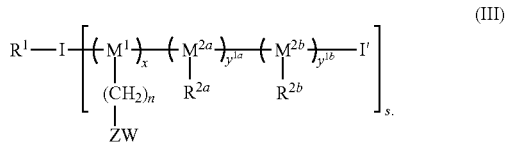

The $R^{2a}$ and $R^{2b}$ groups of formula III are each independently selected from H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, or $L^2$-$LG^2$. The $M^{2a}$ and $M^{2b}$ groups of formula III are each independently selected from acrylate, methacrylate, acrylamide, methacrylamide, styrene, vinyl-pyridine or vinyl-pyrrolidone. Subscripts $y^{1a}$ and $y^{1b}$ of formula III are each independently an integer of from 1 to 1000. Additional comonomers $M^2$ can be present in the random copolymers of the present invention, such as $M^{2c}$, $M^{2d}$, $M^{2e}$, $M^{2f}$, $M^{2g}$, $M^{2h}$, etc., where each comonomer is present in a same or different $y^1$ value, and each comonomer having a corresponding $R^2$ group attached, $R^{2c}$, $R^{2d}$, $R^{2e}$, $R^{2f}$, $R^{2g}$, $R^{2h}$, etc., respectively.

The different monomers of the random copolymers can also be present in any suitable ratio. For example, the $M^2$ monomers, collectively or individually, can be present relative to the $M^1$ monomer in a ratio of 100:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50 and 1:100. In addition, each $M^2$ monomer can be present in any suitable ratio relative to the $M^1$ or any other $M^2$ monomer, such as 100:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50 and 1:100.

The random copolymers of the present invention can have any suitable architecture. For example, the random copolymers can be linear or branched. When the random copolymers are branched, they can have any suitable number of copolymer arms, as defined by subscript s of formula I, such as 2, 3, 4, 5, 6, 7, 8, 9, 10, 20, 30, 40, 50, 60, 70, 80, 90 and up to 100 arms. In some embodiments, subscript s can be from 1 to 20, 1 to 15, 1 to 10, 1 to 9, 1 to 8, 1 to 7, 1 to 6, 1 to 5, 1 to 4, 1 to 3 or 1 to 2. The random copolymers of the present invention can adopt any suitable architecture. For example, the random copolymers can be linear, branched, stars, dendrimers, combs, etc.

A functional agent of the random copolymers can be linked to either one of the comonomers $M^2$, or to the initiator fragment I, or both. When multiple functional agents are present, a functional agent can be linked to both the comonomer $M^2$ and the initiator fragment I. In some embodiments, the random copolymer has formula IIa:

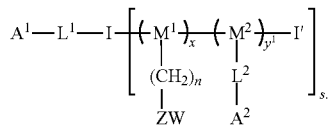

(IIa)

In formula IIa, functional agent $A^1$ can be a drug or therapeutic protein and functional agent $A^2$ can be a targeting agent. Alternatively, functional agent $A^1$ can be a targeting agent and functional agent $A^2$ can be a drug or therapeutic protein. Furthermore, functional agents $A^1$ and $A^2$ can both be therapeutic agents. Moreover, the linkers $L^1$ and $L^2$ can be the same or different. For example, linker $L^1$ can be a cleavable linker, such as when attached to a drug or therapeutic protein to facilitate release of the drug or therapeutic protein, while linker $L^2$ can be a non-cleavable linker, such as when attached to a targeting agent. Furthermore, linker $L^1$ can be a non-cleavable linker, while linker $L^2$ can be a cleavable linker. Alternatively, both linkers $L^1$ and $L^2$ can be cleavable linkers or non-cleavable linkers. In addition, the linker attached to the targeting agent can also be a cleavable linker.

When multiple comonomers $M^2$ are present, each comonomer $M^2$ can have a different functional agent attached. For example, the random copolymer can have formula IIIa:

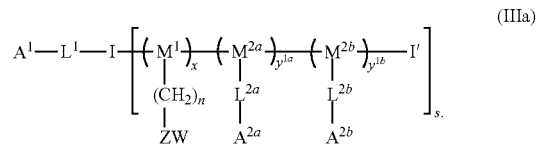

(IIIa)

The groups $L^{2a}$ and $L^{2b}$ of formula IIIa are each a linker. And the groups $A^{2a}$ and $A^{2b}$ of formula IIIa are each a functional agent. Functional agents $A^{2a}$ and $A^{2b}$ can be the same or different in formula IIIa. Functional agent $A^{2a}$ can be a drug or therapeutic protein and functional agent $A^{2b}$ can be a targeting agent. Alternatively, functional agents $A^{2a}$ and $A^{2b}$ can both be targeting agents, and functional agent $A^1$ can be the drug or therapeutic agent. The functional agents $A^{2a}$ and $A^{2b}$ can also both be a drug or therapeutic agent, while functional agent $A^1$ is the targeting agent. When functional agents $A^{2a}$ and $A^{2b}$ are both a drug or therapeutic agent, each functional agent $A^{2a}$ and $A^{2b}$ can be a different drug or therapeutic agent. In addition, one of functional agents $A^{2a}$ and $A^{2b}$ can be a drug or therapeutic agent and the other can be a targeting agent, where functional agent $A^1$ can be any functional agent.

As described above for formula IIa, the linkers $L^1$, $L^{2a}$ and $L^{2b}$ of formula IIIa can be the same or different. For example, linker $L^1$ can be a cleavable linker when attached to a drug or therapeutic agent to facilitate release of the drug or therapeutic agent, while linkers $L^{2a}$ and $L^{2b}$ can be non-cleavable linkers when attached to targeting agents. Alternatively, linker $L^1$ can also be a non-cleavable linker and linkers $L^{2a}$ and $L^{2b}$ can be cleavable linkers. Furthermore, linkers $L^{2a}$ and $L^{2b}$ can be the same or different, such as where one is a cleavable linker and the other is a non-cleavable linker. Linkers $L^{2a}$ and $L^{2b}$ can also be different cleavable linkers, such as when each is attached to a drug, to provide different release rates for the different drugs.

In some embodiments, there is no functional agent linked to the initiator fragment I, such as in formula IIIb:

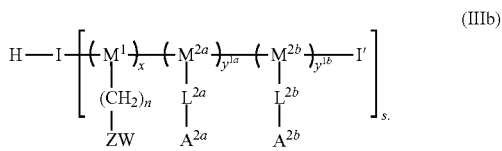

(IIIb)

The groups $L^{2a}$ and $L^{2b}$ of formula IIIb are each a linker. And the groups $A^{2a}$ and $A^{2b}$ of formula IIIb are each a functional agent. In formula IIIb, functional agents $A^{2a}$ and $A^{2b}$ can be the same or different, as described above, and linkers $L^{2a}$ and $L^{2b}$ can be the same or different. In other embodiments, one of the comonomers $M^2$ can have no functional agent or linking group, such as in formula IIIc:

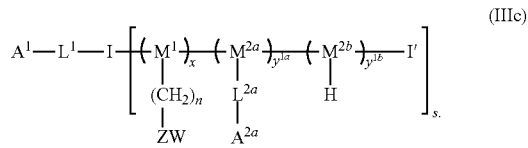

(IIIc)

When additional comonomers, $M^2$ are present in the random copolymers of the present invention, the corresponding linkers $L^2$ can be the same or different as linkers $L^1$, $L^{2a}$ and $L^{2b}$, as described above. Moreover, the corresponding functional agents $A^2$ can be the same or different as functional agents $A^1$, $A^{2a}$ and $A^{2b}$, as described above.

In some embodiments, the random copolymers have linking groups LG linked to either or both of the initiator fragment I and the comonomers $M^2$, such as shown in the structures below:

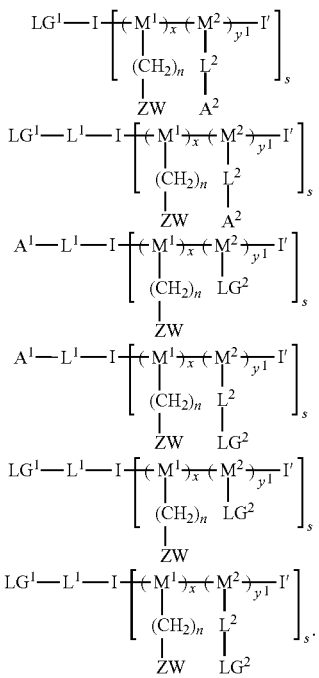

The linking groups $LG^2$ facilitate the "clicking" on of functional agents and initiator groups following polymerization.

When a plurality of comonomers $M^2$ is present, the comonomers can be linked to either a functional agent or a linking group, for example as shown in the following formula:

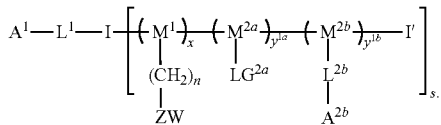

In addition, the linking group can be present on the initiator fragment I while functional agents $A^2$ are linked to the comonomers $M^2$. Alternatively, when the linking group LG is linked to the initiator fragment I, a second linking group LG can be linked to one of the comonomers $M^2$:

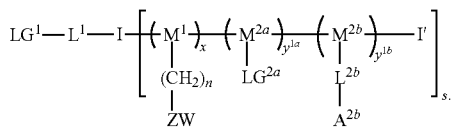

Moreover, a functional agent $A^1$ can be linked to the initiator fragment I while linking groups LG are linked to the comonomers $M^2$, where the linking groups can be the same or different:

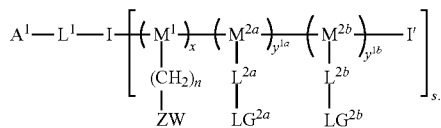

In some embodiments when there are multiple comonomers $M^2$, one of the comonomers $M^2$ can be linked to a group other than a linking group LG, a functional agent A or an initiator I. In other embodiments, at least one $R^2$ group is H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. For example, such structures include the following:

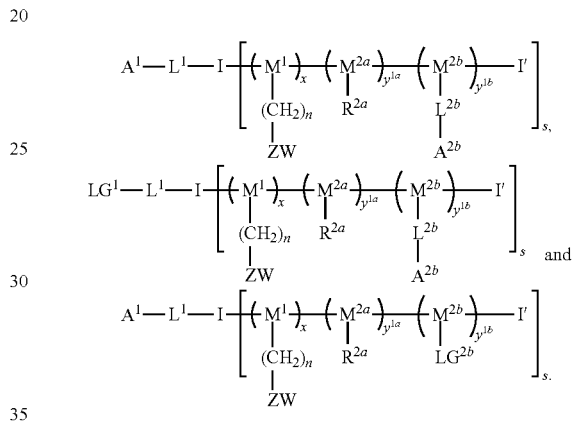

wherein $R^{2a}$ can be H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. In other embodiments, $R^{2a}$ can be a species having one or more positive or negative charges, such as aspartic acid, glutamic acid, lysine, histidine, arginine, choline or hyaluronic acid.

When $R^2$ of some comonomers $M^2$ is the initiator $I^2$, more complex architectures can be prepared of the random copolymers. For example, comb polymers, hyperbranched polymers and dendrimers can be prepared. When initiator $I^2$ is present on a comonomer $M^2$, polymerization using initiator $I^2$ typically occurs following polymerization using initiator I-I'. In some embodiments, polymerization via I-I' and $I^2$ can be simultaneous. Moreover, the initiator $I^2$ can be linked to the comonomer $M^2$ via a cleavable or non-cleavable linker $L^2$.

In some embodiments, the random copolymers of the present invention can be modified via a subsequent polymerization with one or more additional monomers. For example, in formula III above, monomers $M^1$ and $M^{2a}$ can be copolymerized in a first polymerization, and monomer $M^{2b}$ can be polymerized in a second polymerization. A block copolymer would be formed having two blocks, the first block being a random copolymer of $M^1$ and $M^{2a}$, and the second block a homopolymer of $M^{2b}$. Alternatively, following polymerization of monomers $M^1$ and $M^{2a}$, monomer $M^{2b}$ can be copolymerized with monomer $M^{2c}$, thus forming a block copolymer where the first block is a random copolymer of $M^1$ and $M^{2a}$, and the second block a random copolymer of $M^{2b}$ and $M^{2c}$. Additional polymer structures can be prepared by copolymerizing monomers $M^1$, $M^{2a}$ and $M^{2b}$ in a first polymerization, followed by copolymerization of monomers $M^{2c}$, $M^{2d}$, and others, in a second copolymerization. Additional blocks can be prepared by yet a third polymerization using additional monomers. Such polymers provide blocks of copolymers that can have different properties, drugs and functional agents.

A. Initiators

The random copolymers of the present invention are polymerized using any suitable initiator. Initiators useful in the present invention can be described by the formula: I-(I')$_m$, where subscript m is an integer from 1 to 20. The initiator fragment I can be any group that initiates the polymerization. The initiator fragment I' can be any group that will reversibly terminate the growing polymer chain. The initiator fragment I' can be a halogen such as bromine, allowing the end of the polymer to be functionalized after polymerization. In addition, the initiator fragment I can optionally be functionalized with an $R^1$ group that can include a variety of functional groups to tune the functionality of the random copolymer.

Initiators useful in the present invention can have a single initiator fragment I', or any suitable number of branches such that there are multiple initiator fragments I' each capable of reversibly terminating a growing polymer chain. When the initiator fragment I is branched and is capable of initiating multiple polymer chains, subscript m is greater than one such that there are as many initiator fragments I' as there are growing polymer chains.

The bond between initiator fragments I and I' is labile, such that during the polymerization process monomers $M^1$ and comonomers $M^2$ are inserted between initiator fragments I and I'. For example, during a free radical polymerization, such as ATRP, initiator fragments I and I' dissociate, as shown in FIG. 1, to form radicals of I and I'. The radical of initiator fragment I then reacts with the monomers in solution to grow the polymer and forms a propagating polymer radical (species A and species C of FIG. 1). During the polymerization process, the radical of initiator fragment I' will reversibly react with the propagating polymer radical to temporarily stop polymer growth. The bond between the monomer and the initiator fragment I' is also labile, such that the bond can cleave and allow the propagating polymer radical to react with additional monomer to grow the polymer. The end result of the polymerization process is that initiator fragment I is at one end of the polymer chain and initiator fragment I' is at the opposite end of the polymer chain.

The radical of initiator fragment I is typically on a secondary or tertiary carbon, and can be stabilized by an adjacent carbonyl carbon. The initiator fragment I' is typically a halogen, such as bromine, chlorine or iodine. Together, initiator fragments I and I' form the initiators $I^1$ and $I^2$ useful in the preparation of the random copolymers of the present invention.

A broad variety of initiators can be used to prepare the random copolymers of the invention, including a number of initiators set forth in U.S. Pat. No. 6,852,816 (incorporated herein by reference). In some embodiments, the initiators employed for ATRP reactions to prepare random copolymers of the invention are selected from alkanes, cycloalkanes, alkyl carboxylic acids or esters thereof, cycloalkylcarboxylic acids or esters thereof, ethers and cyclic alkyl ethers, alkyl aryl groups, alkyl amides, alkyl-aryl carboxylic acids and esters thereof, and also bearing one initiator fragment I' where unbranched random copolymers are prepared, and more than one initiator fragment I' where branched molecules are prepared.

Initiator fragments I' useful in the present invention include, but are not limited to, halogens, such as Br, Cl and I, thiocyanate (—SCN) and isothiocyanate (—N═C═S). Other groups are useful for the initiator fragment I' of the present invention. In some embodiments, the initiator fragment I' is bromine.

Initiators employed for ATRP reactions can be hydroxylated. In some embodiments, the initiators employed for ATRP reactions to prepare random copolymers of the invention are selected from alkanes, cycloalkanes, alkyl carboxylic acids or esters thereof, cycloalkylcarboxylic acids or esters thereof, ethers, cyclic alkyl ethers, alkyl aryl groups, alkyl amides, alkyl-aryl carboxylic acids and esters thereof, bearing a hydroxyl group, and also bearing one initiator fragment I' where unbranched random copolymers are to be prepared, or alternatively, more than one initiator fragment I' where branched molecules are to be prepared.

Initiators employed for ATRP reactions can bear one or more amine groups. In some embodiments, the initiators employed for ATRP reactions to prepare random copolymers of the invention are alkanes, cycloalkanes, alkyl carboxylic acids or esters thereof, cycloalkylcarboxylic acids or esters thereof, ethers, cyclic alkyl ethers alkyl aryl groups, alkyl amides, alkyl-aryl carboxylic acids and esters thereof, bearing an amine group and also bearing one initiator fragment I' where unbranched random copolymers are to be prepared, or alternatively, more than one initiator fragment I' where branched molecules are to be prepared.

Alkylcarboxylic acids, including alkyl dicarboxylic acids, having at least one initiator fragment I', and substituted with amino or hydroxy groups can also be employed as initiators. In some embodiments of the invention where ATRP is employed to prepare random copolymers of the present invention, the initiators can be alkylcarboxylic acids bearing one or more halogens selected from chlorine and bromine.

Alkanes substituted with two or more groups selected from —COOH, —OH and —NH$_2$, and at least one initiator fragment I', can also be employed as initiators for the preparation of random copolymers where ATRP is employed to prepare random copolymers of the present invention.

Initiators can also contain one or more groups including, but not limited to, —OH, amino, monoalkylamino, dialkylamino, —O-alkyl, —COOH, —COO-alkyl, or phosphate groups (or protected forms thereof).

A broad variety of initiators are commercially available, for example bromoacetic acid N-hydroxysuccinimide ester available from Sigma-Aldrich (St. Louis, Mo.). Suitably protected forms of those initiators can be prepared using standard methods in the art as necessary.

Other initiators include thermal, redox or photo initiator, including, for example, alkyl peroxide, substituted alkyl peroxides, aryl peroxides, substituted aryl peroxides, acyl peroxides, alkyl hydroperoxides, substituted aryl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, azo compounds and halide compounds. Specific initiators include cumene hydroperoxide (CHP), tert-butyl hydroperoxide (TBHP), tert-butyl perbenzoate, (TBPB), sodium carbonateperoxide, benzoyl peroxide (BPO), lauroyl peroxide (LPO), methylethyl ketone 45%, potassium persulfate, ammonium persulfate, 2,2-azobis (2,4-dimethyl-valeronitrile), 1,1-azobis(cyclo-hexanecarbonitrile), 2,2-azobis(N,N-dimethyleneisobutyramidine)dihydrochloride, and 2,2-azobis(2-amido-propane) dihydrochloride. Redox pairs such as persulfate/sulfite and Fe (2+) peroxide or ammonium persulfate and N,N,N'N'-tetramethylethylenediamine (TEMED).

Still other initiators useful for preparing the random copolymers of the present invention, are branched. Suitable initiators having a single branch point include the following:

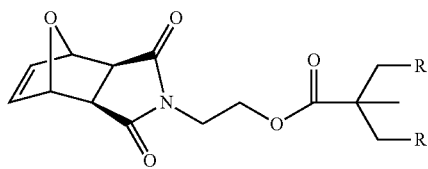

where radical R can be any of the following:

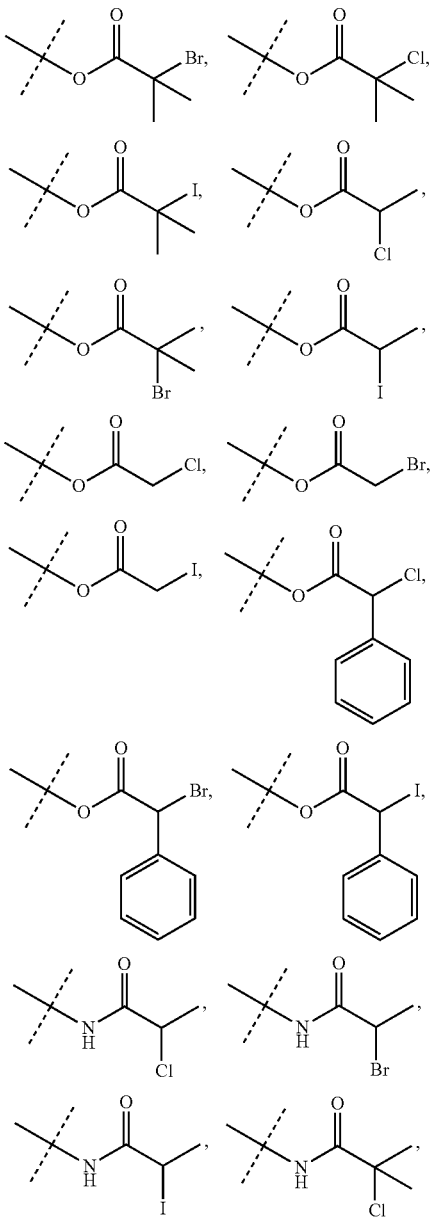

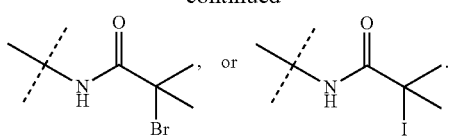

In some embodiments, the initiator can be:

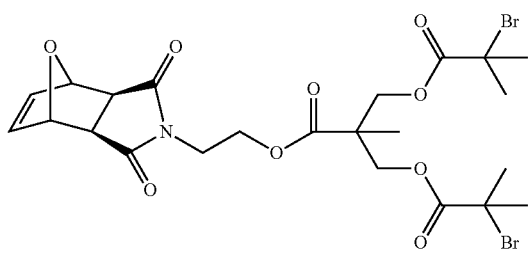 [SMILES: CC(C)(Br)C(=O)OCC(C)(COC(=O)C(C)(C)Br)C(=O)OCCN1C(=O)[C@@H]2C3C=CC(O3)[C@@H]2C1=O]

which is a protected maleimide that can be deprotected after polymerization to form the maleimide for reaction with additional functional groups.

Additional branched initiators include, but are not limited to, the following, where radical R is as defined above:

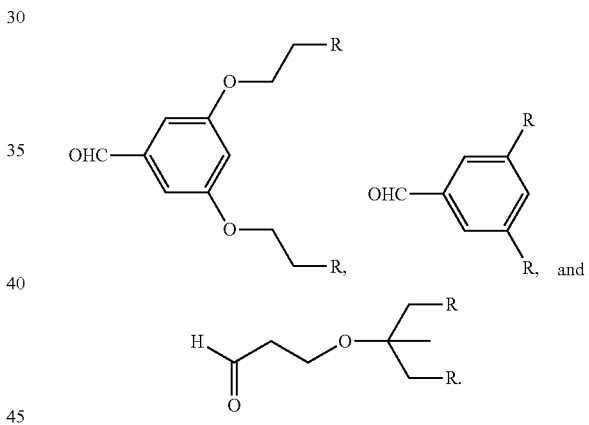

In some embodiments, the branched initiators include, but are not limited to, the following:

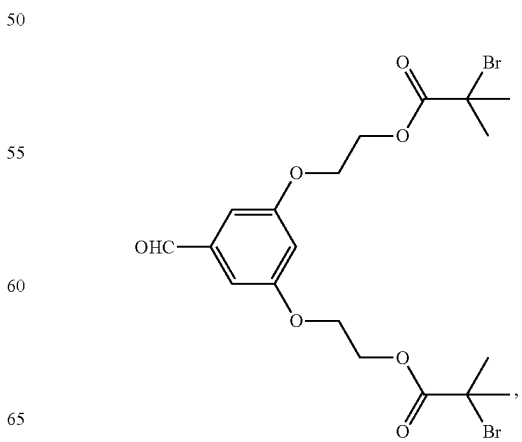

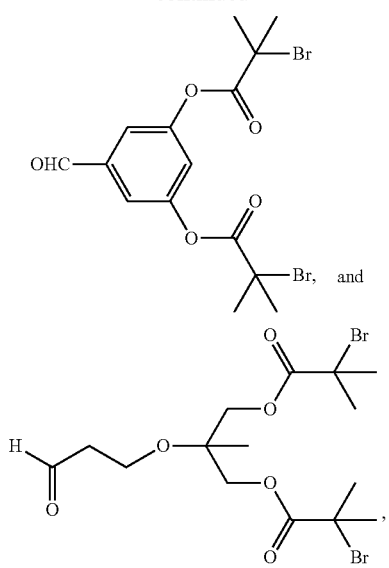

Other branched initiators useful for preparing the random copolymers of the present invention include the following:

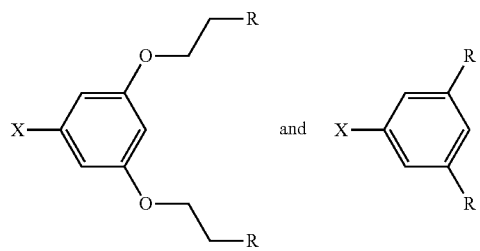

where radical R is as defined above, and radical X can be CHO, SO$_2$Cl, SO$_2$CH=CH$_2$, NHCOCH$_2$I, N=C=O and N=C=S, among others. Additional X groups can include the

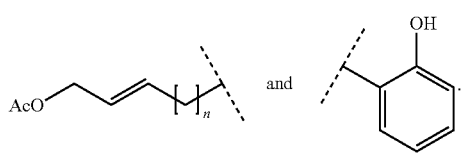

Still other initiators include, but are not limited to, the following:

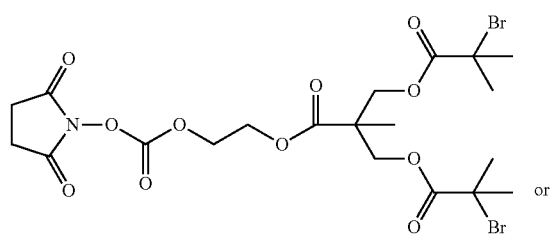

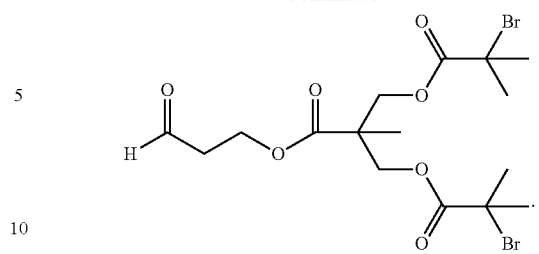

In other embodiments, the initiator can have several branch points to afford a plurality of polymer arms, such as:

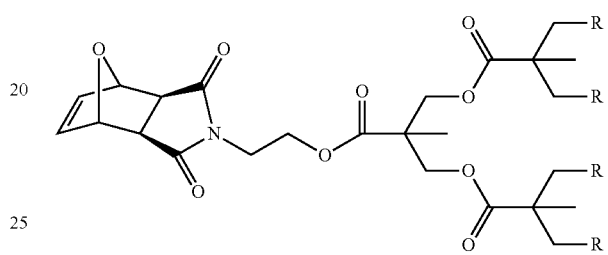

where radical R is as defined above. In some other embodiments, the initiator can have the following structure:

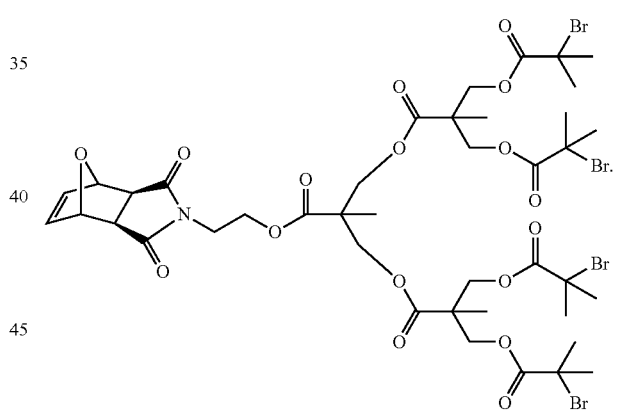

As described above, the initiator can be added to the polymerization mixture separately, or can be incorporated into another molecule, such as a monomer (hyperbranched structure) or a polymer fragment (such as graft copolymers). Initiation of the polymerization can be accomplished by heat, UV light, or other methods known to one of skill in the art.

B. Monomers

Monomers useful for preparing the random copolymers of the present invention include any monomer capable of radical polymerization. Typically, such monomers have a vinyl group. Suitable monomers include, but are not limited to, acrylate, methacrylate, acrylamide, methacrylamide, styrene, vinyl-pyridine and vinyl-pyrrolidone monomers. Monomers, M$^1$, containing the zwitterionic moiety, ZW, include, but are not limited to, the following:

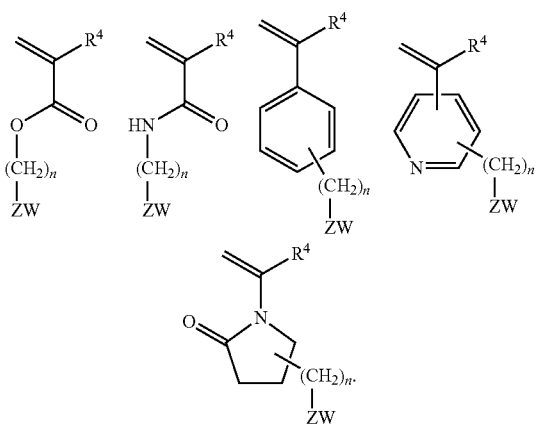

Monomers, $M^2$, containing the linking group or functional agent include, but are not limited to, the following structures:

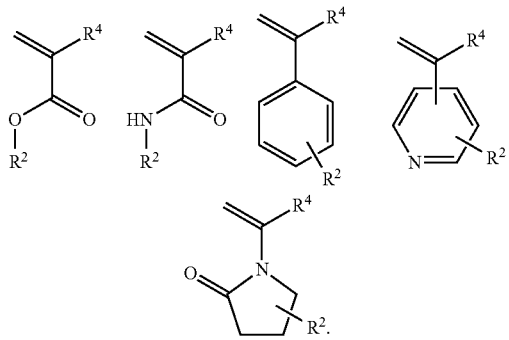

Other monomers are well-known to one of skill in the art, and include vinyl acetate and derivatives thereof.

In some embodiments, the monomers are acrylate or methacrylate monomers. In other embodiments, the random copolymer has the formula:

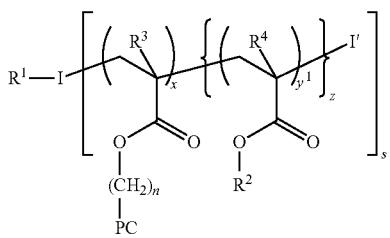

wherein the groups $R^3$ and $R^4$ are independently selected from H or $C_{1-6}$ alkyl, and PC is phosphatidylcholine. In some other embodiments, the random copolymer has the formula:

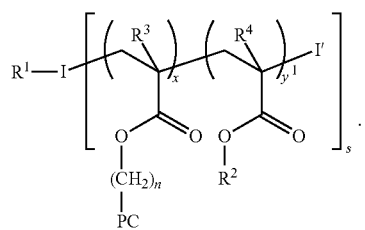

In still other embodiments, the random copolymer has the formula:

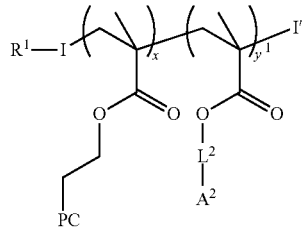

wherein $A^2$ is camptothecin.

In other embodiments, the random copolymer has the formula:

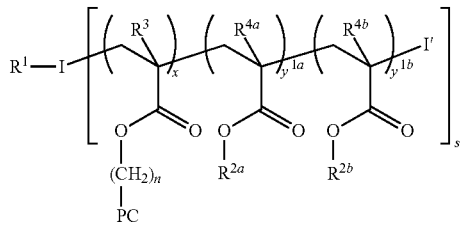

wherein $R^{2a}$ and $R^{2b}$ are each independently selected from H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$; $LG^2$, or $L^2$-$LG^2$; each of $R^3$, $R^{4a}$ and $R^{4b}$ are independently selected from H or $C_{1-6}$ alkyl; subscripts $y^{1a}$ and $y^{1b}$ are each independently an integer of from 1 to 1000; and PC is phosphatidylcholine. In still yet other embodiments, the random copolymer can have the following formula:

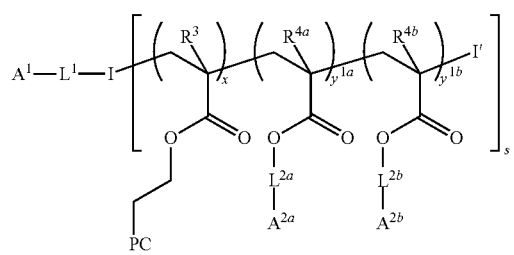

wherein each of $L^{2a}$ and $L^{2b}$ is a linker, and each of $A^{2a}$ and $A^{2b}$ is a functional agent. In other embodiments, the random copolymer can have the following formula:

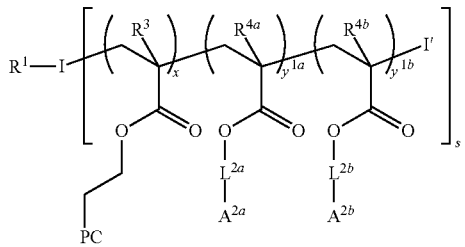

wherein each of $L^{2a}$ and $L^{2b}$ is a linker, and each of $A^{2a}$ and $A^{2b}$ is a functional agent.

C. Zwitterions

The zwitterions of the present invention include any compound having both a negative charge and a positive charge.

Groups having a negative charge and suitable for use in the zwitterions of the present invention include, but are not limited to, phosphate, sulfate, other oxoanions, etc. Groups having a positive charge and suitable for use in the zwitterions of the present invention include, but are not limited to, ammonium ions. In some embodiments, the zwitterion can be phosphorylcholine.

D. Linkers

The random copolymers of the present invention can also incorporate any suitable linker L. The linkers provide for attachment of the functional agents to the initiator fragment I and the comonomers $M^2$. The linkers can be cleavable or non-cleavable, homobifunctional or heterobifunctional. Other linkers can be both heterobifunctional and cleavable, or homobifunctional and cleavable.

Cleavable linkers include those that are hydrolyzable linkers, enzymatically cleavable linkers, pH sensitive linkers, disulfide linkers and photolabile linkers, among others. Hydrolyzable linkers include those that have an ester, carbonate or carbamate functional group in the linker such that reaction with water cleaves the linker. Enzymatically cleavable linkers include those that are cleaved by enzymes and can include an ester, amide, or carbamate functional group in the linker. pH sensitive linkers include those that are stable at one pH but are labile at another pH. For pH sensitive linkers, the change in pH can be from acidic to basic conditions, from basic to acidic conditions, from mildly acidic to strongly acidic conditions, or from mildly basic to strongly basic conditions. Suitable pH sensitive linkers are known to one of skill in the art and include, but are not limited to, ketals, acetals, imines or imminiums, siloxanes, silazanes, silanes, maleamates-amide bonds, ortho esters, hydrazones, activated carboxylic acid derivatives and vinyl ethers. Disulfide linkers are characterized by having a disulfide bond in the linker and are cleaved under reducing conditions. Photolabile linkers include those that are cleaved upon exposure to light, such as visible, infrared, ultraviolet, or electromagnetic radiation at other wavelengths.

Other linkers useful in the present invention include those described in U.S. Patent Application Nos. 2008/0241102 (assigned to Ascendis/Complex Biosystems) and 2008/0152661 (assigned to Mirus) (incorporated in their entirety herein). Mirus linkers useful in the present invention include, but are not limited to, the following:

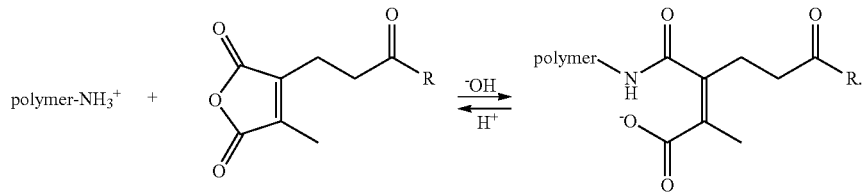

Other linkers include those described in *Bioconjugate Techniques*, Greg T. Hermanson, Academic Press, 2d ed., 2008 (incorporated in its entirety herein), and those described in Angew. Chem. Int. Ed. 2009, 48, 6974-6998 (Bertozzi, C. R. and Sletten, E. M) (incorporated in its entirety herein).

In some embodiments, linkers $L^1$ and $L^2$ can have a length of up to 30 atoms, each atom independently C, N, O, S, and P. In other embodiments, the linkers $L^1$ and $L^2$ can be any of the following: —$C_{1-12}$ alkyl-, —$C_{3-12}$ cycloalkyl-, —($C_{1-8}$ alkyl)-($C_{3-12}$ cycloalkyl)-($C_{0-8}$ alkyl)-, —$(CH_2)_{1-12}$O—, (—$(CH_2)_{1-6}$—O—$(CH_2)_{1-6}$—)$_{1-12}$—, (—$(CH_2)_{1-4}$—NH—$(CH_2)_{1-4}$)$_{1-12}$—, (—$(CH_2)_{1-4}$—O—$(CH_2)_{1-4}$)$_{1-12}$—O—, (—$(CH_2)_{1-4}$—O—$(CH_2)_{1-4}$)$_{1-12}$—O—$(CH_2)_{1-12}$—, —$(CH_2)_{1-12}$—(C=O)—O—, —$(CH_2)_{1-12}$—O—(C=O)—, -(phenyl)-$(CH_2)_{1-3}$—(C=O)—O—, -(phenyl)-$(CH_2)_{1-3}$—(C=O)—NH—, —$(C_{1-6}$ alkyl)-(C=O)—O—$(C_{0-6}$ alkyl)-, —$(CH_2)_{1-12}$—(C=O)—O—$(CH_2)_{1-12}$—, —CH(OH)—CH(OH)—(C=O)—O—CH(OH)—CH(OH)—(C=O)—NH—, —S-maleimido-$(CH_2)_{1-6}$—, —S-maleimido-$(C_{1-3}$ alkyl)-(C=O)—NH—, —S-maleimido-$(C_{1-3}$alkyl)-$(C_{5-6}$ cycloalkyl)-$(C_{0-3}$ alkyl)-, —$(C_{1-3}$ alkyl)-$(C_{5-6}$ cycloalkyl)-$(C_{0-3}$ alkyl)-(C=O)—O—, —$(C_{1-3}$ alkyl)-$(C_{5-6}$ cycloalkyl)-$(C_{0-3}$ alkyl)-(C=O)—NH—, —S-maleimido-$(C_{0-3}$alkyl)-phenyl-$(C_{0-3}$alkyl)-, —$(C_{0-3}$ alkyl)-phenyl-(C=O)—NH—, —$(CH_2)_{1-12}$—NH—(C=O)—, —$(CH_2)_{1-12}$—(C=O)—NH—, (phenyl)-$(CH_2)_{1-3}$—(C=O)—NH—, —S—$(CH_2)$—(C=O)—NH-(phenyl)-, —$(CH_2)_{1-12}$—(C=O)—NH—$(CH_2)_{1-12}$—, —$(CH_2)_2$—(C=O)—O—$(CH_2)_2$—O—(C=O)—$(CH_2)_2$—(C=O)—NH—, —$(C_{1-6}$ alkyl)-(C=O)—N—$(C_{1-6}$ alkyl)-, acetal, ketal, acyloxyalkyl ether, —N=CH—, —$(C_{1-6}$ alkyl)-S—S—$(C_{0-6}$ alkyl)-, —$(C_{1-6}$ alkyl)-S—S—$(C_{1-6}$ alkyl)-(C=O)—O—, —$(C_{1-6}$ alkyl)-S—S—$(C_{1-6}$ alkyl)-(C=O)—NH—, —S—S—$(CH_2)_{1-3}$—(C=O)—NH—$(CH_2)_{1-4}$—NH—(C=O)—$(CH_2)_{1-3}$—, —S—S—$(C_{0-3}$ alkyl)-(phenyl)-, —S—S—$(C_{1-3}$-alkyl)-(phenyl)-(C=O)—NH—$(CH_2)_{1-5}$—, —$(C_{1-3}$ alkyl)-(phenyl)-(C=O)—NH—$(CH_2)_{1-5}$—(C=O)—NH—, —S—S—$(C_{1-3}$-alkyl)-, —$(C_{1-3}$-alkyl)-(phenyl)-(C=O)—NH—, —O—$(C_1$-$C_6$ alkyl)-S$(O_2)$—$(C_{1-6}$ alkyl)-O—(C=O)—NH—, —S—S—$(CH_2)_{1-3}$—(C=O)—, —$(CH_2)_{1-3}$—(C=O)—NH—N=C—S—S—$(CH_2)_{1-3}$—(C=O)—NH—$(CH_2)_{1-5}$—, —$(CH_2)_{1-3}$—(C=O)—NH—$(CH_2)_{1-5}$—(C=O)—NH—, —$(CH_2)_{0-3}$-(heteroaryl)-$(CH_2)_{0-3}$—, —$(CH_2)_{0-3}$-phenyl-$(CH_2)_{0-3}$—, —N=C(R)—, —$(C_{1-6}$ alkyl)-C(R)=N—$(C_{1-6}$ alkyl)-, —$(C_{1-6}$ alkyl)-(aryl)-C(R)=N—$(C_{1-6}$ alkyl)-, —$(C_{1-6}$ alkyl)-C(R)=N-(aryl)-$(C_{1-6}$ alkyl)-, and —$(C_{1-6}$alkyl)-O—P(O)(OH)—O—$(C_{0-6}$alkyl)-, wherein R is H, $C_{1-6}$ alkyl, $C_{3-6}$ cycloalkyl, or an aryl group having 5-8 endocyclic atoms.

In some other embodiments, linkers $L^1$ and $L^2$ can be any of the following: —$C_1$-$C_{12}$ alkyl-, —$C_3$-$C_{12}$ cycloalkyl-, (—$(CH_2)_{1-6}$—O—$(CH_2)_{1-6}$—)$_{1-12}$—, (—$(CH_2)_{1-4}$—NH—$(CH_2)_{1-4}$)$_{1-12}$—, —$(CH_2)_{1-12}$O—, (—$(CH_2)_{1-4}$—O—$(CH_2)_{1-4}$)$_{1-12}$—O—, —$(CH_2)_{1-12}$—(CO)—O—, —$(CH_2)_{1-12}$—(CO)—NH—, —$(CH_2)_{1-12}$—O—(CO)—, —$(CH_2)_{1-12}$—NH—(CO)—, (—$(CH_2)_{1-4}$—O—$(CH_2)_{1-4}$)$_{1-12}$—O—$(CH_2)_{1-12}$—, —$(CH_2)_{1-12}$—(CO)—O—$(CH_2)_{1-12}$—, —$(CH_2)_{1-12}$—(CO)—NH—$(CH_2)_{1-12}$—, —$(CH_2)_{1-12}$—O—(CO)—$(CH_2)_{1-12}$—, —$(CH_2)_{1-12}$—NH—(CO)—$(CH_2)_{1-12}$—, —$(C_3$-$C_{12}$ cycloalkyl)-, —$(C_1$-$C_8$alkyl)-$(C_3$-$C_{12}$ cycloalkyl)-, —$(C_3$-$C_{12}$ cycloalkyl)-$(C_{1-8}$ alkyl)-, —$(C_{1-8}$alkyl)-$(C_3$-$C_{12}$ cycloalkyl)-$(C_{1-8}$alkyl)-, and —$(CH_2)_{0-3}$-aryl-$(CH_2)_{0-3}$—.

In still other embodiments, each of linkers $L^1$ and $L^2$ is a cleavable linker independently selected from hydrolyzable linkers, enzymatically cleavable linkers, pH sensitive linkers, disulfide linkers and photolabile linkers.

E. Linking Groups LG

The linkers and functional agents of the present invention can react with a linking group on the initiator fragment I or the comonomers $M^2$ to form a bond. The linking groups LG of the present invention can be any suitable functional group capable of forming a bond to another functional group, thereby linking the two groups together. For example, linking groups LG useful in the present invention include those used in click chemistry, maleimide chemistry, and NHS-esters, among others. Linking groups involved in click chemistry include, but are not limited to, azides and alkynes that form a triazole ring via the Huisgen cycloaddition process (see U.S. Pat. No. 7,375,234, incorporated herein in its entirety). The maleimide chemistry involves reaction of the maleimide olefin with a nucleophile, such as —OH, —SH or —NH$_2$, to form a stable bond. Other linking groups include those described in *Bioconjugate Techniques*, Greg T. Hermanson, Academic Press, 2d ed., 2008 (incorporated in its entirety herein).

Some non-limiting examples of the reaction of the linking groups and some groups typically found or introduced into functional agents are set forth in Table I.

TABLE I

| Illustrative Groups that may react with a linking group (LG) | Exemplary Reactive Linking Groups (shown as appended to -X) | Product Y-X |
| --- | --- | --- |
| Y-COOH | HO-X (hydroxyl or activated forms thereof (e.g., tresylate, mesylate etc.)) | Y-C(=O)O-X |
| Y-COOH | HS-X (thiol) | Y-C(=O)S-X |
| Y-SH | | Y-S—S-X |
| Y-SH | R'-S—S-X (disulfide) | Y-S—S-X |
| Y-SH | (pyridyl)-S—S-X (dithiopyridyl) | Y-S—S-X |
| Y-NH$_2$ | H(O=)C-X aldehyde | Y-N=CH-X or Y-NH—CH$_2$-X following reduction |
| Y-NH$_2$ | (HO)$_2$HC-X aldehyde hydrate | Y-N=CH-X or Y-NH—CH$_2$-X following reduction |
| Y-NH$_2$ | (R'O)$_2$CH-X or 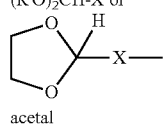 acetal | Y-N=CH-X or Y-NH—CH$_2$-X following reduction |
| Y-NH$_2$ | R'OCH(OH)-X or hemiacetal | Y-N=CH-X or Y-NH—CH-X following reduction |
| Y-NH$_2$ | R'(O=)C-X ketone | Y-N=CR'-X or Y-NH—C(R')H-X following reduction |
| Y-NH$_2$ | (R'O)$_2$C(R')-X or 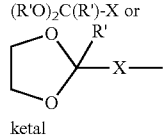 ketal | Y-N=C(R')-X or Y-NH—C(R')H-X following reduction |
| Y-NH$_2$ | R'OC(R')(OH)-X hemiketal | Y-N=C(R')-X or Y-NH—C(R')H-X following reduction |
| Y-NH$_2$ | R'(S=)C-X ketone thione (thioketone) | Y-N=C(R')-X or Y-NH—C(R')H-X following redcuction |
| Y-NH$_2$ | (R'O)(R'S)C(R')-X or 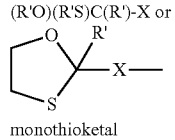 monothioketal | Y-N=C(R')-X or Y-NH—C(R')H-X following reduction |

TABLE I-continued

| Illustrative Groups that may react with a linking group (LG) | Exemplary Reactive Linking Groups (shown as appended to -X) | Product Y-X |
|---|---|---|
| Y-NH$_2$ | R'SC(R')(SH)-X<br>dithiohemiketal | Y-N=C(R')-X<br>or<br>Y-NH—C(R')H-X following reduction |
| Y-NH$_2$ | (R'S)$_2$C(R')-X or<br>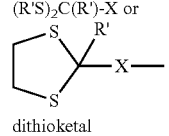<br>dithioketal | Y-N=C(R')-X<br>or<br>Y-NH—C(R')H-X following reduction |
| Y-SH<br>Y-OH<br>Y-COOH (anion)<br>Y-NHR" | 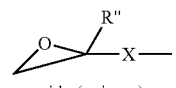<br>epoxide (oxirane) | Y-S—CH$_2$—C(OH)(R")-X-<br>Y-O—CH$_2$—C(OH)(R")-X-<br>Y-C(=O)O—CH$_2$—C(OH)(R")-X-<br>Y-NR"-CH$_2$—C(OH)(R")-X- |
| Y-SH<br>Y-OH<br>Y-COOH (anion)<br>Y-NHR" | 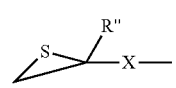<br>thioepoxide | Y-S—CH$_2$—C(SH)(R")-X<br>Y-O—CH$_2$—C(SH)(R")-X-<br>Y-C(=O)O—CH$_2$—C(SH)(R")-X-<br>Y-NR"-CH$_2$—C(SH)(R")-X- |
| Y-SH<br>Y-OH<br>Y-NHR"<br>Y-SH<br>Y-OH<br>Y-NHR" | HO—(C=O)-X<br>carboxyl<br><br>(alcohol)-(C=O)-X<br>carboxylic acid ester<br>(alcohol indicates an esterified suitable alcohol leaving group e.g., p-nitrophenyl) | Y-S—(C=O)-X<br>Y-O—(C=O)-X<br>Y-N(R")-(C=O)-X<br>Y-S—(C=O)-X<br>Y-O—(C=O)-X<br>Y-NR"-(C=O)-X |
| Y-NH$_2$ | 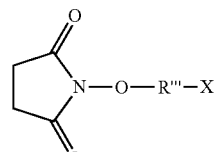<br>N-hydroxysuccinimide ester | Y-NH-R'''-X |
| Y-SH | 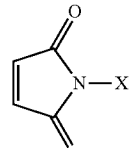 | 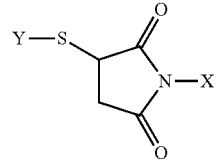 |
| Y-NH$_2$ | 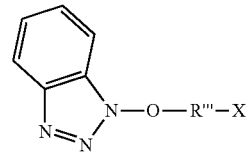<br>1-benzotriazole ester | Y-NH-R'''-X |
| Y-NH$_2$<br>Y-(C=NH)—O—((CH$_2$)$_{1-3}$)—CH$_3$<br>(imidoester)<br>Y-COOH<br>Y-(C=O)-R"<br>Y-COOH<br>Y-(C=O)-R" | CH$_3$—((CH$_2$)$_{1-3}$)—O(C=NH)-X<br>(imidoester)<br>H$_2$N-X<br><br>H$_2$N-X<br>amine<br><br>H$_2$N—(C=O)—NH-X<br>urea | Y-NH—(C=NH)-X<br>(amidine)<br>Y-(C=NH)—HN-X<br>(amidine)<br>Y-(C=O)—NH-X<br><br>Y-(R")C=N-X or<br>Y-(R")CH—NH-X following reduction<br>Y(C=O)—NH—(C=O)—NH-X<br>Y-(R")C=N—(C=O)—NH-X or<br>Y-(R")CH—NH—(C=O)—NH-X following reduction |

TABLE I-continued

| Illustrative Groups that may react with a linking group (LG) | Exemplary Reactive Linking Groups (shown as appended to -X) | Product Y-X |
|---|---|---|
| Y-COOH | $H_2N-(C=O)-O-X$<br>carbamate | $Y-(C=O)-NH-(C=O)-O-X$ |
| Y-(C=O)-R" |  | $Y-(R")C=N-(C=O)-O-X$ or<br>$Y-(R")CH-NH(C=O)-O-X$<br>following reduction |
| Y-COOH | $H_2N-(C=S)-NH-X$<br>thiourea | $Y-(C=O)-NH-(C=S)-NH-X$ |
| Y-(C=O)-R" |  | $Y-(R")C=N-(C=S)-NH-X$ or<br>$Y-(R")CH-NH-(C=S)-NH-X$<br>following reduction |
| Y-COOH | $H_2N-(C=S)-O-X$<br>thiocarbamate | $Y-(C=O)-NH-(C=S)-O-X$ |
| Y-(C=O)-R" |  | $Y-(R")C=N-(C=S)-O-X$ or<br>$Y-(R")CH-NH-(C=S)-O-X$<br>following reduction |
| Y-(C=O)-R" | $H_2N-HN-X$ | $Y-(R")C=N-HN-X$<br>hydrazone |
| $Y-NH-NH_2$ | $R"-(O=C)-X$ | $Y-NH-N=C(R")-X$<br>hydrazone |
| $Y-NH_2$ | $O=C=N-X$<br>isocyanate | $Y-NH-(C=O)-NH-X$ |
| Y-OH |  | $Y-O-(C=O)-NH-X$ |
| $Y-NH_2$ | $S=C=N-X$<br>isothiocyanate | $Y-NH-(C=S)-NH-X$ |
| Y-OH |  | $Y-O-(C=S)-NH-X$ |
| Y-SH | $H_2C=CH-(C=O)-X$<br>or<br>$H_2C=C(CH_3)-(C=O)-X$<br>alpha-beta unsubstituted carbonyls | $Y-S-CH_2CH_2-(C=O)-X$<br>$Y-S-CH_2-CH(CH_3)-(C=O)-X$ |
| Y-SH | $H_2C=CH-(C=O)O-X$<br>alpha-beta unsubstituted carboxyl | $Y-S-CH_2CH_2-(C=O)O-X$ |
| Y-SH | $H_2C=C(CH_3)-(C=O)-O-X$<br>alpha-beta unsubstituted carboxyls (methacrylates) | $Y-S-CH_2CH(CH_3)-(C=O)O-X$ |
| Y-SH | $H_2C=CH-(C=O)NH-X$<br>alpha-beta unsubstituted amides (acrylamides) | $Y-S-CH_2CH_2-(C=O)NH-X$ |
| Y-SH | vinylpyridine-X<br>(2- or 4-vinylpyridine) | $Y-S-CH_2-CH_2-(pyridyl)-X$ |
| Y-SH | $H_2C=CH-SO_2-X$<br>(vinyl sulfone) | $Y-S-H_2C-CH_2-SO_2-X$ |
| Y-SH | $ClH_2C-CH_2-SO_2-L$<br>(chloroethyl sulfone) | $Y-S-H_2C-CH_2-SO_2-X$ |
| Y-SH | $(halogen)-CH_2-(C=O)-O-X$<br>$(halogen)-CH_2-(C=O)-NH-X$<br>$(halogen)CH_2-(C=O)-X$<br>(halogen is preferably I or Br) | $Y-S-CH_2-(C=O)-O-X$<br>$Y-S-CH_2-(C=O)-NH-X$<br>$Y-S-CH_2-(C=O)-X$ |
| $Y-O(C=O)-CH_2$-(halogen)<br>$Y-NH(C=O)-CH_2$-(halogen)<br>$Y-(C=O)-CH_2$-(halogen)<br>(halogen is preferably I or Br) | HS-X | $Y-O(C=O)-CH_2-S-X$<br>$Y-NH(C=O)-CH_2-S-X$<br>$Y-(C=O)-CH_2-S-X$ |
| Y-SH | $(halogen)-CH_2(C=O)O-X$<br>$(halogen)-CH_2(C=O)NH-X$<br>$(halogen)-CH_2(C=O)-X$<br>(halogen is preferably I or Br) | $Y-S-CH_2(C=O)O-X$<br>$Y-S-CH_2(C=O)NH-X$<br>$Y-S-CH_2(C=O)-X$ |
| $Y-N_3$ | $HC\equiv C-X$ | ![triazole] Y-N(triazole ring)-X |
| Y-SH | aziridine-X (H-N ring with X) | $Y-S-CH_2-CH(NH_2)-X$ |
| $Y-NH_2$ | $(F_5-Ph)-OC(O)-X$ | $Y-NH-C(O)-X$ |

R' is $C_{1-6}$ alkyl, $C_{3-6}$ cycloalkyl, or an aryl group having 5-8 endocyclic atoms;

R" is H, $C_{1-6}$ alkyl, $C_{3-6}$ cycloalkyl, or an aryl group having 5-8 endocyclic atoms;

R'" is a carbonyl derivative *—(C=O)—, *—(C=O)—(CH$_2$)$_{1-8}$—S—S—, *—(C=O)—(CH$_2$)$_{1-8}$—(C=O)—O—, *—(C=O)—(CH$_2$)$_{1-8}$—O—(C=O)—, *—(C=O)—(CH$_2$)$_{1-8}$—(C=O)—NH—, or *—(C=O)—(CH$_2$)$_{1-8}$—NH—(C=O)—, or alternatively, R'" is carbonyl derivative of the form *—(C=O)—O—(CH$_2$)$_{1-8}$—S—S—, *—(C=O)—O—(CH$_2$)$_{1-8}$—(C=O)—O—, *—(C=O)—O—(CH$_2$)$_{1-8}$—O—(C=O)—, *—(C=O)—O—(CH$_2$)$_{1-8}$—(C=O)—NH—, or *—(C=O)—O—(CH$_2$)$_{1-8}$—NH—(C=O)—, where "*" indicates the point of attachment to succinimidyl or benzotriazolyl groups;

X and Y are each the active agent, linker, monomer or initiator fragment I.

—C(O)NR$^{1a}$R$^{1b}$, —NR$^{1a}$R$^{1b}$, $C_{1-6}$ alkyl-NR$^{1a}$R$^{1b}$, —N(R$^{1a}$)C(O)R$^{1b}$, —N(R$^{1a}$)C(O)OR$^{1b}$, —N(R$^{1a}$)C(O)NR$^{1a}$R$^{1b}$, —OP(O)(OR$^{1a}$)$_2$, —S(O)$_2$OR$^{1a}$, —S(O)$_2$NR$^{1a}$R$^{1b}$, —CN, —NO$_2$, cycloalkyl, heterocycloalkyl, aryl and heteroaryl F. Functional Agents Functional agents useful in the random copolymers of the present invention include any biological agent or synthetic compound capable of targeting a particular ligand, receptor, complex, organelle, cell, tissue, epithelial sheet, or organ, or of treating a particular condition or disease state. Of particular interest, is a combination of bioactive agents that together target mechanisms common to a particular disease. For example, a first bioactive agent (stably attached) that is a biopharmaceutical agent that binds to a protein upregulated in a disease; a second bioactive agent (stably attached) that is a peptide that binds to an extracellular matrix tissue constituent such as heparin sulfate; a third bioactive agent (unstably attached) that is a small molecule drug that releases over time and exerts a local, intracellular effect, for example, an antiproliferative effect. In some embodiments, the bioactive agent is a drug, a therapeutic protein, a small molecule, a peptide, a peptoid, an oligonucleotide (aptamer, siRNA, microRNA), a nanoparticle, a carbohydrate, a lipid, a glycolipid, a phospholipid, or a targeting agent. The ratio of comonomers is chosen based on predefined stoichiometry (for example, to match a biological avidity; to match a biological stoichiometry; to impart a 'gearing' effect). Other functional agents useful in the random copolymers of the present invention include, but are not limited to, radiolabels, fluorophores and dyes.

The functional agents can be linked to the initiator fragment I or the comonomers M$^2$, or both, of the random copolymers. The functional agents can be linked to the initiator fragment I or the comonomers M$^2$ either before or after polymerization via cleavable or non-cleavable linkers described above. The functional agent can also be physisorbed or ionically absorbed to the random copolymer instead of covalently attached.

The preparation of the random copolymers of the present invention linked to a functional agent can be conducted by first linking the functional agent to a linking group attached to a monomer and subjecting the coupled functional agent to conditions suitable for synthesis of the inventive random copolymers. In those cases, a suitable linking group can be an initiator (e.g., iodinated, brominated or chlorinated compound/group) for use in ATRP reactions. Such a reaction scheme is possible where the functional agent is compatible with the polymer polymerization reactions and any subsequent workup required. However, coupling of functional agents to preformed random copolymers can be used where the functional agent is not compatible with conditions suitable for polymerization. In addition, where cost makes the loss of an agent to imperfect synthetic yields, oftentimes encountered particularly in multistep synthetic reactions, coupling of functional agent to preformed random copolymers of the present invention can be employed.

Where a functional agent is not compatible with the conditions employed for polymerization reactions, it can be desirable to introduce the functional agent subsequent to the polymerization reaction.

Bioactive agents, A, can be broadly selected. In some embodiments the bioactive agents can be selected from one or more drugs, vaccines, aptamers, avimer scaffolds based on human A domain scaffolds, diabodies, camelids, shark IgNAR antibodies, fibronectin type III scaffolds with modified specificities, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, microRNA, DNA, cDNA, antisense constructs, ribozymes, etc, and combinations thereof). In one embodiment, the bioactive agents can be selected from proteins, peptides, polypeptides, soluble or cell-bound, extracellular or intracellular, kinesins, molecular motors, enzymes, extracellular matrix materials and combinations thereof. In another embodiment, bioactive agents can be selected from nucleotides, oligonucleotides, polynucleotides, and nucleic acids (e.g., mRNA, tRNA, snRNA, RNAi, DNA, cDNA, antisense constructs, ribozymes etc and combinations thereof). In another embodiment, bioactive agents can be selected from steroids, lipids, fats and combinations thereof. For example, the bioactive agent can bind to the extracellular matrix, such as when the extracellular matrix is hyaluronic acid or heparin sulfate proteoglycan and the bioactive agent is a positively charged moiety such as choline for non-specific, electrostatic, Velcro type binding interactions. In another embodiment, the bioactive agent can be a peptide sequence that binds non-specifically or specifically.

Bioactive agents can be designed and/or selected to have a full activity (such as a high level of agonism or antagonism). Alternatively, a multifunctional bioactive agent can be selected to modulate one target protein's activity while impacting fully another.

Just as mosaic proteins contain extracellular binding domains or sub-domains (example, VEGF and Heparin Binding Epidermal Growth Factor), sequences from these binding sites can be replicated as a bioactive agent for polymer attachment. More broadly, mosaic proteins represent strings of domains of many functions (target binding, extracellular matrix binding, spacers, avidity increases, enzymatic). The set of bioactives chosen for a particular application can be assembled in similar fashion to replicate a set of desired functional activities.

Other functional agents, A, include charged species such as choline, lysine and hyaluronic acid, among others. The charged species are useful for facilitating ionic attachment, to vitreous for example.

Therapeutic Proteins and Antibodies

In one particularly useful embodiment, the functional agent is a therapeutic protein. Numerous therapeutic proteins are disclosed throughout the application such as, and without limitation, erythropoietin, granulocyte colony stimulating factor (G-CSF), GM-CSF, interferon alpha, interferon beta, human growth hormone, and imiglucerase.

In one embodiment, the functional agents can be selected from specifically identified polysaccharide, protein or peptide bioactive agents, including, but not limited to: Aβ, agalsidase, alefacept, alkaline phosphatase, aspariginase, amdoxovir (DAPD), antide, becaplermin, botulinum toxin including types A and B and lower molecular weight compounds with botulinum toxin activity, calcitonins, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, N-Acetylgalactosamine-6-sulfate sulfatase, collagen, cyclosporin, alpha defensins, beta defensins, desmopressin, exendin-4, cytokines, cytokine receptors, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, parathyroid hormone, parathyroid hormone related peptide, OP-1; acidic fibroblast growth factor, basic fibroblast growth factor, Fibroblast Growth Factor 21, CD-40 ligand, heparin, human serum albumin, low molecular weight heparin (LMWH), interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-17, interleukin-21, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, kelix-imab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$tositumomab, trastuzumab, tuvirumab, visilizumab, and fragments and mimetics thereof.

In one embodiment, the bioactive agent is a fusion protein. For example, and without limitation, the bioactive component can be an immunoglobulin or portion of an immunoglobulin fused to one or more certain useful peptide sequences. For example, the bioactive agent may contain an antibody Fc fragment. In one embodiment, the bioactive agent is a CTLA4 fusion protein. For example, the bioactive agent can be an Fc-CTLA4 fusion protein.

In one particularly useful embodiment, the bioactive agent is a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Therefore, in one embodiment, the bioactive agent is the human form of each of the proteins and polypeptides disclosed herein for which there is a human form. Examples of such human proteins include, without limitation, human antibodies, human enzymes, human hormones and human cytokines such as granulocyte colony stimulation factor, granulocyte macrophage colony stimulation factor, interferons (e.g., alpha interferons and beta interferons), human growth hormone and erythropoietin.

Other examples of therapeutic proteins which may serve as bioactive agents include, without limitation, factor VIII, b-domain deleted factor VIII, factor VIIa, factor IX, anticoagulants; hirudin, alteplase, tpa, reteplase, tpa, tpa-3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-apha1, consensus ifn, ifn-beta, ifn-beta 1b, ifn-beta 1a, ifn-gamma (e.g., 1 and 2), ifn-lambda, ifn-delta, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone. And any of these can be modified to have a site-specific conjugation point (a N-terminus, or C-terminus, or other location) using natural (for example, a serine to cysteine substitution) (for example, formylaldehyde per method of Redwood Biosciences) or non-natural amino acid.

Examples of therapeutic antibodies that may serve as bioactive agents include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-$\beta_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Proteins, Peptides and Amino Acids

Proteins and peptides for use as bioactive agents as disclosed herein can be produced by any useful method including production by in vitro synthesis and by production in biological systems. Typical examples of in vitro synthesis methods which are well known in the art include solid-phase synthesis ("SPPS") and solid-phase fragment condensation ("SPFC"). Biological systems used for the production of proteins are also well known in the art. Bacteria (e.g., *E. coli* and *Bacillus* sp.) and yeast (e.g., *Saccharomyces cerevisiae* and *Pichia pastoris*) are widely used for the production of heterologous proteins. In addition, heterologous gene expression for the production of bioactive agents for use as disclosed herein can be accomplished using animal cell lines such as mammalian cell lines (e.g., CHO cells). In one particularly useful embodiment, the bioactive agents are produced in transgenic or cloned animals such as cows, sheep, goats and birds (e.g., chicken, quail, ducks and turkey), each as is understood in the art. See, for example, U.S. Pat. No. 6,781,030, issued Aug. 24, 2004, the disclosure of which is incorporated in its entirety herein by reference.

Bioactive agents such as proteins produced in domesticated birds such as chickens can be referred to as "avian derived" bioactive agents (e.g., avian derived therapeutic proteins). Production of avian derived therapeutic proteins is known in the art and is described in, for example, U.S. Pat. No. 6,730,822, issued May 4, 2004, the disclosure of which is incorporated in its entirety herein by reference.

In embodiments where the bioactive agent is a protein or polypeptide, functional groups present in the amino acids of the protein polypeptide sequence can be used to link the agent to the random copolymer. Linkages to protein or polypeptide bioactive agents can be made to naturally occurring amino acids in their sequence or to naturally occurring amino acids that have either been added to the sequence or inserted in place of another amino acid, for example the replacement of a serine by a cysteine.

Protein or polypeptide bioactive agents may also comprise non-naturally occurring amino acids in addition to the common naturally occurring amino acids found in proteins and polypeptides. In addition to being present for the purpose of altering the properties of a polypeptide or protein, non-naturally occurring amino acids can be introduced to provide a functional group that can be used to link the protein or polypeptide directly to random copolymer. Furthermore, naturally occurring amino acids, e.g., cysteine, tyrosine, tryptophan can be used in this way.

Non-naturally occurring amino acids can be introduced into proteins and peptides by a variety of means. Some of the techniques for the introduction of non-natural amino acids are discussed in U.S. Pat. No. 5,162,218, the disclosure of which is incorporated in its entirety herein by reference. First, non-naturally occurring amino acids can be introduced by chemical modification of a polypeptide or protein on the amino acid side chain or at either the amino terminus or the carboxyl terminus. Non-limiting examples of chemical modification of a protein or peptide might be methylation by agents such as diazomethane, or the introduction of acetylation at an amino group present in lysine's side chain or at the amino terminus of a peptide or protein. Another example of the protein/polypeptide amino group modification to prepare a non-natural amino acid is the use of methyl 3-mercaptopropionimidate ester or 2-iminothiolane to introduce a thiol (sulfhydryl, —SH) bearing functionality linked to positions in a protein or polypeptide bearing a primary amine. Once introduced, such groups can be employed to form a covalent linkage to the protein or polypeptide.

Second, non-naturally occurring amino acids can be introduced into proteins and polypeptides during chemical synthesis. Synthetic methods are typically utilized for preparing polypeptides having fewer than about 200 amino acids, usually having fewer than about 150 amino acids, and more usually having 100 or fewer amino acids. Shorter proteins or polypeptides having less than about 75 or less than about 50 amino acids can be prepared by chemical synthesis.

The synthetic preparation methods that are particularly convenient for allowing the insertion of non-natural amino acids at a desired location are known in the art. Suitable synthetic polypeptide preparation methods can be based on Merrifield solid-phase synthesis methods where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

Examples of non-naturally occurring amino acids that can be introduced during chemical synthesis of polypeptides include, but are not limited to: D-amino acids and mixtures of D and L-forms of the 20 naturally occurring amino acids, N-formyl glycine, ornithine, norleucine, hydroxyproline, beta-alanine, hydroxyvaline, norvaline, phenylglycine, cyclohexylalanine, t-butylglycine (t-leucine, 2-amino-3,3-dimethylbutanoic acid), hydroxy-t-butylglycine, amino butyric acid, cycloleucine, 4-hydroxyproline, pyroglutamic acid (5-oxoproline), azetidine carboxylic acid, pipecolinic acid, indoline-2-carboxylic acid, tetrahydro-3-isoquinoline carboxylic acid, 2,4-diaminobutyricacid, 2,6-diaminopimelic acid, 2,4-diaminobutyricacid, 2,6-diaminopimelicacid, 2,3-diaminopropionicacid, 5-hydroxylysine, neuraminic acid, and 3,5-diiodotyrosine.

Third, non-naturally occurring amino acids can be introduced through biological synthesis in vivo or in vitro by insertion of a non-sense codon (e.g., an amber or ocher codon) in a DNA sequence (e.g., the gene) encoding the polypeptide at the codon corresponding to the position where the non-natural amino acid is to be inserted. Such techniques are discussed for example in U.S. Pat. Nos. 5,162,218 and 6,964,859, the disclosures of which are incorporated in their entirety herein by reference. A variety of methods can be used to insert the mutant codon including oligonucleotide-directed mutagenesis. The altered sequence is subsequently transcribed and translated, in vivo or in vitro in a system which provides a suppressor tRNA, directed against the nonsense codon that has been chemically or enzymatically acylated with the desired non-naturally occurring amino acid. The synthetic amino acid will be inserted at the location corresponding to the nonsense codon. For the preparation of larger and/or glycosylated polypeptides, recombinant preparation techniques of this type are usually preferred. Among the amino acids that can be introduced in this fashion are: formyl glycine, fluoroalanine, 2-Amino-3-mercapto-3-methylbutanoic acid, homocysteine, homoarginine and the like. Other similar approaches to obtain non-natural amino acids in a protein include methionine substitution methods.

Where non-naturally occurring amino acids have a functionality that is susceptible to selective modification, they are particularly useful for forming a covalent linkage to the protein or polypeptide. Circumstances where a functionality is susceptible to selective modification include those where the functionality is unique or where other functionalities that might react under the conditions of interest are hindered either stereochemically or otherwise.

Drugs

In another embodiment, the bioactive agents can also be selected from specifically identified drug or therapeutic agents, including but not limited to: tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines. Bioactive agents may also be selected from the group consisting of aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine in another embodiment.

Other bioactive agents useful in the present invention include extracellular matrix targeting agents, functional transport moieties and labeling agents. Extracellular matrix targeting agents include, but are not limited to, heparin binding moieties, matrix metalloproteinase binding moieties, lysyl oxidase binding domains, negatively charged moieties or positively charged moieties and hyaluronic acid. Functional transport moieties include, but are not limited to, blood brain barrier transport moieties, intracellular transport moieties, organelle transport moieties, epithelial transport domains and tumor targeting moieties (folate, other). In some embodiments, the targeting agents useful in the present invention target anti-TrkA, anti A-beta (peptide 1-40, peptide 1-42, monomeric form, oligomeric form), anti-IGF1-4, agonist RANK-L, anti-ApoE4 or anti-ApoA1, among others.

Diagnostic Agents

Diagnostic agents useful in the random copolymers of the present invention include imaging agents and detection agents such as radiolabels, fluorophores, dyes and contrast agents.

Imaging agent refers to a label that is attached to the random copolymer of the present invention for imaging a tumor, organ, or tissue in a subject. The imaging moiety can be covalently or non-covalently attached to the random copolymer. Examples of imaging moieties suitable for use in the present invention include, without limitation, radionuclides, fluorophores such as fluorescein, rhodamine, Texas Red, Cy2, Cy3, Cy5, and the AlexaFluor (Invitrogen, Carlsbad, Calif.) range of fluorophores, antibodies, gadolinium, gold, nanomaterials, horseradish peroxidase, alkaline phosphatase, derivatives thereof, and mixtures thereof.

Radiolabel refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}F$) phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 (166Ho), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for meta state. Additionally, naturally occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

Nanoparticles

The functional agents can also include nanoparticles. Nanoparticles useful in the present invention include particles having a size ranging form 1 to 1000 nm. Nanoparticles can be beads, metallic particles or can in some cases be micelles and in some other be liposomes. Other nanoparticles include carbon nanotubes, quantum dots and colloidal gold. Nanoparticles can be packed with diagnostic and/or therapeutic agents.

Those skilled in the art will also recognize that the invention can be used to enable coincident detection of more than one agent of the same or different type. Also, the use of flexible linker chemistries can also be used to witness the loss of one fluorescent label, for example as the molecule is taken up into the cell and into a low pH environment.

IV. Preparation of Phosphoryl-Containing Random Copolymers

The random copolymers of the present invention can be prepared by any means known in the art. In some embodiments, the present invention provides a process for preparing a random copolymer of the present invention, the process including the step of contacting a mixture of a first monomer and a second monomer with an initiator, $I^1$, under conditions sufficient to prepare a random copolymer via free radical polymerization, wherein the first monomer comprises a phosphorylcholine, and each of the second monomer and initiator independently comprise at least one of a functional agent or a linking group for linking to the functional agent.

The mixture for preparing the random copolymers of the present invention can include a variety of other components. For example, the mixture can also include catalyst, ligand, solvent, and other additives. In some embodiments, the mixture also includes a catalyst and a ligand. Suitable catalysts and ligands are described in more detail below.

Any suitable monomer can be used in the process of the present invention, such as those described above.

The random copolymers of the present invention can be prepared by any suitable polymerization method, such as by living radical polymerization. Living radical polymerization, discussed by Odian, G. in Principles of Polymerization, 4$^{th}$, Wiley-Interscience John Wiley & Sons: New York, 2004, and applied to zwitterionic polymers for example in U.S. Pat. No.

6,852,816. Several different living radical polymerization methodologies can be employed, including Stable Free Radical Polymerization (SFRP) and Radical Addition-Fragmentation Transfer (RAFT). In addition, Atom Transfer Radical Polymerization (ATRP), provides a convenient method for the preparation of the random copolymers of the invention.

The preparation of polymers via ATRP involves the radical polymerization of monomers beginning with an initiator bearing one or more halogens. The initiator is activated by a catalyst such as a transition metal salt (CuBr) that can be solubilized by a ligand (e.g., bipyridine). RAFT polymerization uses thiocarbonylthio compounds, such as dithioesters, dithiocarbamates, trithiocarbonates, and xanthates, to mediate the polymerization process via a reversible chain-transfer process. Other living radical processes useful in the preparation of the inventive random copolymers include nitroxide-mediated polymerization.

Initiators

Initiators useful for the preparation of the random copolymers of the present invention include any initiator suitable for polymerization via atom transfer radical polymerization (ATRP), such as those described above. Other useful initiators include those for nitroxide mediated radical polymerization (NMP), or reversible addition-fragmentation-termination (RAFT or MADIX) polymerization. Still other techniques to control a free-radical polymerization process can be used, such as the use of iniferters, degenerative transfer or telomerization process. Moreover, the initiators useful in the present invention include those having at least one branch point, such as those described above.

Random copolymers of the present invention having complex architectures including branched compounds having multiple polymer arms including, but not limited to, comb and star structures. Comb architectures can be achieved employing linear initiators bearing three or more halogen atoms, preferably the halogens are chlorine, bromine, or iodine atoms, more preferably the halogens are chlorine or bromine atoms. Star architectures can also be prepared employing compounds bearing multiple halogens on a single carbon atom or cyclic molecules bearing multiple halogens. In some embodiments compounds having star architecture have 3 polymer arms and in other embodiments they have 4 polymer arms. See initiators described above.

Catalyst and Ligands

Catalyst for use in ATRP or group radical transfer polymerizations may include suitable salts of $Cu^{1+}$, $Cu^{2+}$, $Fe^{2+}$, $Fe^{3+}$, $Ru^{2+}$, $Ru.^{3+}$, $Cr^{2+}$, $Cr^{3+}$, $Mo^{2+}$, $Mo.^{3+}$, $W^{2+}$, $W^{3+}$, $Mn^{2+}$, $Mn^{2+}$, $Mn^{4+}$, $Rh^{3+}$, $Rh^{4+}$, $Re^{2+}$, $Re^{3+}$, $Co^{1+}$, $Co.^{2+}$, $Co^{3+}$, $V^{2+}$, $V^{3+}$, $Zn.^{1+}$, $Zn^{2+}$, $Ni^{2+}$, $Ni^{3+}$, $Au^{1+}$, $Au^{2+}$, $Ag^{1+}$ and $Ag^{2+}$. Suitable salts include, but are not limited to: halogen, $C_1$-$C_6$-alkoxy, sulfates, phosphate, triflate, hexafluorophosphate, methanesulphonate, arylsulphonate salts. In some embodiments the catalyst is a chloride, bromide salts of the above-recited metal ions. In other embodiments the catalyst is CuBr, CuCl or $RuCl_2$.

In some embodiments, the use of one or more ligands to solubilize transition metal catalysts is desirable. Suitable ligands are usefully used in combination with a variety of transition metal catalysts including where copper chloride or bromide, or ruthenium chloride transition metal salts are part of the catalyst. The choice of a ligand affects the function of catalyst as ligands not only aid in solubilizing transition metal catalysts in organic reaction media, but also adjust their redox potential. Selection of a ligand is also based upon the solubility and separability of the catalyst from the product mixture. Where polymerization is to be carried out in a liquid phase soluble ligands/catalyst are generally desirable although immobilized catalysts can be employed. Suitable ligands include those pyridyl groups (including alkyl pyridines e.g., 4.4. dialkyl-2,2' bipyridines) and pyridyl groups bearing an alkyl substituted imino group, where present, longer alkyl groups provide solubility in less polar monomer mixtures and solvent media. Triphenyl phosphines and other phosphorus ligands, in addition to indanyl, or cyclopentadienyl ligands, can also be employed with transition metal catalysts (e.g., $Ru^{+2}$-halide or $Fe^{+2}$-halide complexes with triphenylphosphine, indanyl or cyclopentadienyl ligands).

An approximately stoichiometric amount of metal compound and ligand in the catalyst, based on the molar ratios of the components when the metal ion is fully complexed, is employed in some embodiments. In other embodiments the ratio between metal compound and ligand is in the range 1:(0.5 to 2) or in the range 1:(0.8 to 1.25).

Generally, where the catalyst is copper, bidentate or multidentate nitrogen ligands produce more active catalysts. In addition, bridged or cyclic ligands and branched aliphatic polyamines provide more active catalysts than simple linear ligands. Where bromine is the counter ion, bidentate or one-half tetradentate ligands are needed per $Cu^{+1}$. Where more complex counter ions are employed, such as triflate or hexafluorophosphate, two bidentate or one tetradentate ligand can be employed. The addition of metallic copper can be advantageous in some embodiments particularly where faster polymerization is desired as metallic copper and $Cu^{+2}$ may undergo redox reaction to form $Cu^{+1}$. The addition of some $Cu^{+2}$ at the beginning of some ATRP reactions can be employed to decrease the amount of normal termination.

In some embodiments, the amount of catalyst employed in the polymerization reactions is the molar equivalent of the initiator that is present. Since catalyst is not consumed in the reaction, however, it is not essential to include a quantity of catalyst as high as of initiator. The ratio of catalyst to initiator, based on transition metal compound in some embodiments is from about 1:(1 to 50), and in other embodiments from about 1:(1 to 10).

Polymerization Conditions

In some embodiments, the living radical polymerization process of the invention is preferably carried out to achieve a degree of polymerization in the range of 3 to about 2000, and in other embodiments from about 5 to about 500. The degree of polymerization in other embodiments is in the range 10 to 100, or alternatively in the range of about 10 to about 50. The degree of polymerization in group or atom transfer radical polymerization technique, is directly related to the initial ratio of initiator to monomer. Therefore, in some embodiments the initial ratios of initiator to monomer are in the range of 1:(3 to about 2,000) or about 1:(5 to 500), or about 1:(10 to 100), or about 1:(10 to 50).

Polymerization reactions are typically carried out in the liquid phase, employing a single homogeneous solution. The reaction may, however, be heterogeneous comprising a solid and a liquid phase (e.g., a suspension or aqueous emulsion). In those embodiments where a non-polymerizable solvent is employed, the solvent employed is selected taking into consideration the nature of the zwitterionic monomer, the initiator, the catalyst and its ligand; and in addition, any comonomer that can be employed.

The solvent may comprise a single compound or a mixture of compounds. In some embodiments the solvent is water, and in other embodiments water is present in an amount from about 10% to about 100% by weight, based on the weight of the monomers present in the reaction. In those embodiments where a water insoluble comonomer is to be polymerized with a zwitterionic monomer, it can be desirable to employ a solvent or co-solvent (in conjunction with water) that permits solubilization of all the monomers present. Suitable organic solvents include, without limitation, formamides (e.g., dimethylformamide), ethers (e.g., tetrahydrofuran), esters (ethyl acetate) and, most preferably, alcohols. In some embodiments where a mixture of water and organic solvent is to be employed, $C_1$-$C_4$ water miscible alkyl alcohols (methanol, ethanol, propanol, isopropanol, butanol, isobutanol, and tertbutanol) are useful organic solvents. In other embodiments, water and methanol combinations are suitable for conducting polymerization reactions. The reaction may also be conducted in supercritical solvents such as $CO_2$.

As noted above, in some embodiments it is desirable to include water in the polymerization mixture in an amount from about 10% to about 100% by weight based on the weight of monomers to be polymerized. In other embodiments the total non-polymerizable solvent is from about 1% to about 500% by weight, based on the weight of the monomers present in the reaction mixture. In other embodiments, the total non-polymerizable solvent is from about 10% to about 500% by weight or alternatively from 20% to 400%, based on the weight of the monomers present in the reaction mixture. It is also desirable in some cases to manipulate the solubility of an input reagent, such as initiator or monomer, for example by modifying temperature or solvent or other method so as to modify the reaction conditions in a dynamic fashion.

In some embodiments, contact time of the zwitterionic monomer and water prior to contact with the initiator and catalyst are minimized by forming a premix comprising all components other than the zwitterionic monomer and for the zwitterionic monomer to be added to the premix last.

The polymerization reactions can be carried out at any suitable temperature. In some embodiments the temperature can be from about ambient (room temperature) to about 120° C. In other embodiments the polymerizations can be carried out at a temperature elevated from ambient temperature in the range of about 60° to 80° C. In other embodiments the reaction is carried out at ambient (room temperature).

In some embodiments, the compounds of the invention have a polydispersity (of molecular weight) of less than 1.5, as judged by gel permeation chromatography. In other embodiments the polydispersities can be in the range of 1.2 to 1.4.

A number of workup procedures can be used to purify the polymer of interest such as precipitation, fractionation, reprecipitation, membrane separation and freeze-drying of the polymers.

Non-Halogenated Polymer Terminus

In some embodiments, it can be desirable to replace the halogen, or other initiator fragment I', with another functionality. A variety of reactions can be employed for the conversion of the aliphatic halogen. In some embodiments, the conversion of the aliphatic halogen can include reaction to prepare an alkyl, alkoxy, cycloalkyl, aryl, heteroaryl or hydroxy group. Halogens can also be subject to an elimination reaction to give rise to an alkene (double bond). Other methods of modifying the halogenated terminus are described in Matyjaszewski et al. *Prog. Polym. Sci.* 2001, 26, 337, incorporated by reference in its entirety herein.

Attachment of Functional Agents

The coupling of functional agents to the random copolymers of the present invention can be conducted employing chemical conditions and reagents applicable to the reactions being conducted. Exemplary methods are described in *Bioconjugate Techniques*, Greg T. Hermanson, Academic Press, 2d ed., 2008 (incorporated in its entirety herein). Other bioconjugation techniques are described in Bertozzi et al. *Angewandte Chemie* 2009, 48, 6974, and Gauthier et al. *Chem. Commun.* 2008, 2591, each incorporated by reference in its entirety herein.

Where, for example, the coupling requires the formation of an ester or an amide, dehydration reactions between a carboxylic acid and an alcohol or amine may employ a dehydrating agent (e.g., a carbodiimide such as dicyclohexylcarbodiimide, DCC, or the water soluble agent 1-ethyl-3-(3-dimethyllaminopropyl)carbodiimide hydrochloride, EDC). Alternatively, N-hydroxysuccinimide esters (NHS) can be employed to prepare amides. Reaction to prepare amides employing NHS esters are typically conducted near neutral pH in phosphate, bicarbonate, borate, HEPES or other nonamine containing buffers at 4° to 25° C. In some embodiments, reactions employing EDC as a dehydrating agent, a pH of 4.5-7.5 can be employed; in other embodiments, a pH of 4.5 to 5 can be employed. Morpholinoethanesulfonic acid, MES, is an effective carbodiimide reaction buffer.

Thiol groups can be reacted under a variety of conditions to prepare different products. Where a thiol is reacted with a maleimide to form a thioether bond, the reaction is typically carried out at a pH of 6.5-7.5. Excess maleimide groups can be quenched by adding free thiol reagents such as mercaptoethanol. Where disulfide bonds are present as a linkage, they can be prepared by thiol-disulfide interchange between a sulfhydryl present in the bioactive group and an X functionality which is a disulfide such as a pyridyl disulfide. Reactions involving pyridyl disulfides can be conducted at pH 4-pH 5 and the reaction can be monitored at 343 nm to detect the released pyridine-2-thione. Thiol groups may also be reacted with epoxides in aqueous solution to yield hydroxy thioethers.

The reaction of guanido groups (e.g., those of an arginine in a protein or polypeptide of interest) with a glyoxal can be carried out at pH 7.0-8.0. The reaction typically proceeds at 25° C. The derivative, which contains two phenylglyoxal moieties per guanido group, is more stable under mildly acidic conditions (below pH 4) than at neutral or alkaline pHs, and permits isolation of the linked materials. At neutral or alkaline pH values, the linkage decomposes slowly. Where an arginine residue of a protein or polypeptide is reacted with a phenylglyoxal reagent, about 80% of the linkage will hydrolyze to regenerate the original arginine residue (in the absence of excess reagent) in approximately 48 hours at 37° at about pH 7.

Imidoester reactions with amines are typically conducted at pH of 8-10, and preferably at about pH 10. The amidine linkage formed from the reaction of an imidoester with an amine is reversible, particularly at high pH.

Haloacetals can be reacted with sulfhydryl groups over a broad pH range. To avoid side reactions between histidine residues that can be present, particularly where the sulfhydryl group is present on a protein or polypeptide, the reaction can be conducted at about pH 8.3.

Aldehydes can be reacted with amines under a variety of conditions to form imines. Where either the aldehyde or the amine is immediately adjacent to an aryl group the product is a Schiff base that tends to be more stable than where no aryl group is present. Conditions for the reaction of amines with aldehydes to form an imine bond include the use of a basic pH from about pH 9 to about pH 11 and a temperature from about 0° C. to room temperature, over 1 to 24 hours. Buffers including borohydride and tertiary amine containing buffers are often employed for the preparation of imines. Where it is desired imine conjugates, which are hydrolytically susceptible, can be reduced to form an amine bond which is not hydrolytically susceptible. Reduction can be conducted with a variety of suitable reducing agents including sodium borohydride or sodium cyanoborohydride.

The reaction conditions provided above are intended to provide general guidance to the artisan. The skilled artisan will recognize that reaction conditions can be varied as necessary to promote the attachment of the functional agent to the random copolymers of the present invention and that guidance for modification of the reactions can be obtained from standard texts in organic chemistry. Additional guidance can be obtained from texts such as Wong, S. S., "Chemistry of Protein Conjugation and Cross-Linking," (CRC Press 1991), which discuss related chemical reactions.

V. Compositions

The present invention includes and provides for pharmaceutical compositions comprising one or more compounds of the invention and one or more pharmaceutically acceptable excipients. The compounds of the invention may be present as a pharmaceutically acceptable salt, prodrug, metabolite, analog or derivative thereof, in the pharmaceutical compositions of the invention. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration.

Pharmaceutically acceptable carriers for use in formulating the random copolymers of the present invention include, but are not limited to: solid carriers such as lactose, terra alba, sucrose, talc, gelatin, agar, pectin, acacia, magnesium stearate, stearic acid and the like; and liquid carriers such as syrups, saline, phosphate buffered saline, water and the like. Carriers may include any time-delay material known in the art, such as glyceryl monostearate or glyceryl distearate, alone or with a wax, ethylcellulose, hydroxypropylmethylcellulose, methylmethacrylate or the like.

Other fillers, excipients, flavorants, and other additives such as are known in the art may also be included in a pharmaceutical composition according to this invention. The use of such media and agents for pharmaceutically active substances is well known in the art. Except insofar as any conventional media or agent is incompatible with the active compound, use thereof in the compositions of the invention is contemplated. Supplementary active compounds can also be incorporated into the compositions of the present invention.

The pharmaceutical preparations encompass all types of formulations. In some embodiments they are parenteral (including subcutaneous, intramuscular, intravenous, intradermal, intraperitoneal, intrathecal, intraventricular, intracranial, intraspinal, intracapsular, and intraosseous) formulations suited for injection or infusion (e.g., powders or concentrated solutions that can be reconstituted or diluted as well as suspensions and solutions). Where the composition is a solid that requires reconstitution or a concentrate that requires dilution with liquid media, any suitable liquid media may be employed. Preferred examples of liquid media include, but are not limited to, water, saline, phosphate buffered saline, Ringer's solution, Hank's solution, dextrose solution, and 5% human serum albumin.

Where a compound or pharmaceutical composition comprising a random copolymer of the present invention is suitable for the treatment of cell proliferative disorders, including but not limited to cancers, the compound or pharmaceutical composition can be administered to a subject through a variety of routes including injection directly into tumors, the blood stream, or body cavities.

While the pharmaceutical compositions may be liquid solutions, suspensions, or powders that can be reconstituted immediately prior to administration, they may also take other forms. In some embodiments, the pharmaceutical compositions may be prepared as syrups, drenches, boluses, granules, pastes, suspensions, creams, ointments, tablets, capsules (hard or soft) sprays, emulsions, microemulsions, patches, suppositories, powders, and the like. The compositions may also be prepared for routes of administration other than parenteral administration including, but not limited to, topical (including buccal and sublingual), pulmonary, rectal, transdermal, transmucosal, oral, ocular, and so forth.

In some embodiments, the pharmaceutical compositions of the present invention comprise one or more random copolymers of the present invention.

Other pharmaceutical compositions of the present invention may comprise one or more random copolymers of the present invention that function as biological ligands that are specific to an antigen or target molecule. Such compositions may comprise a random copolymer of the present invention, where the bioactive agent is a polypeptide that comprises the amino acid sequence of an antibody, or an antibody fragment such as a $FAb_2$ or FAb' fragment or an antibody variable region. Alternatively, the compound may be a random copolymer and the polypeptide may comprise the antigen binding sequence of a single chain antibody. Where a bioactive agent present in a random copolymer of the present invention functions as a ligand specific to an antigen or target molecule, those compounds may also be employed as diagnostic and/or imaging reagents and/or in diagnostic assays.

The amount of a compound in a pharmaceutical composition will vary depending on a number of factors. In one embodiment, it may be a therapeutically effective dose that is suitable for a single dose container (e.g., a vial). In one embodiment, the amount of the compound is an amount suitable for a single use syringe. In yet another embodiment, the amount is suitable for multi-use dispensers (e.g., containers suitable for delivery of drops of formulations when used to deliver topical formulations). A skilled artisan will be able to determine the amount a compound that produces a therapeutically effective dose experimentally by repeated administration of increasing amounts of a pharmaceutical composition to achieve a clinically desired endpoint.

Generally, a pharmaceutically acceptable excipient will be present in the composition in an amount of about 0.01% to about 99.999% by weight, or about 1% to about 99% by weight. Pharmaceutical compositions may contain from about 5% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90% excipient by weight. Other suitable ranges of excipients include from about 5% to about 98%, from about from about 15 to about 95%, or from about 20% to about 80% by weight.

Pharmaceutically acceptable excipients are described in a variety of well known sources, including but not limited to "Remington: The Science & Practice of Pharmacy", 19$^{th}$ ed., Williams & Williams, (1995) and Kibbe, A. H., Handbook of Pharmaceutical Excipients, 3$^{rd}$ Edition, American Pharmaceutical Association, Washington, D.C., 2000.

VI. Methods

The random copolymers of the present invention are useful for treating any disease state or condition. By combining appropriate targeting agents, drugs and therapeutic proteins, along with the phosphorylcholine, the random copolymers of the present invention can be used to address the panoply of mechanisms provided by any one disease state or condition. For example, the disease state or condition can be acute or chronic.

Disease states and conditions that can be treated using the random copolymers of the present invention include, but are not limited to, cancer, autoimmune disorders, genetic disorders, infections, inflammation, and metabolic disorders.

Cancers that can be treated using the random copolymers of the present invention include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, osteogenic sarcomas, fibrosarcoma, neuroblastoma, glioma, melanoma, leukemia, and lymphoma.

In some embodiments, the present invention provides a method of treating cancer, comprising administering a therapeutically effective amount of the random copolymer of formula I to a subject in need thereof, thereby treating cancer. In other embodiments, the random copolymer has formula:

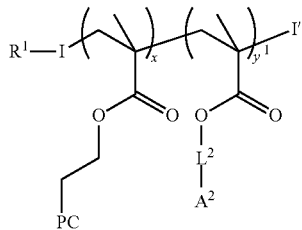

wherein $A^2$ is camptothecin.

Autoimmune diseases that can be treated using the random copolymers of the present invention include, but are not limited to, multiple sclerosis, myasthenia gravis, Crohn's disease, ulcerative colitis, primary biliary cirrhosis, type 1 diabetes mellitus (insulin dependent diabetes mellitus or IDDM), Grave's disease, autoimmune hemolytic anemia, pernicious anemia, autoimmune thrombocytopenia, vasculitides such as Wegener's granulomatosis, Behcet's disease, rheumatoid arthritis, systemic lupus erythematosus (lupus), scleroderma, systemic sclerosis, Guillain-Barre syndromes, Hashimoto's thyroiditis spondyloarthropathies such as ankylosing spondylitis, psoriasis, dermatitis herpetiformis, inflammatory bowel diseases, pemphigus vulgaris and vitiligo.

Some metabolic disorders treatable by the random copolymers of the present invention include lysosomal storage disorders, such as mucopolysaccharidosis IV or Morquio Syndrome, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, hypophosphatasia, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders such as Pseudo-Hurler polydystrophy/Mucolipidosis IIIA, Hurler Syndrome, Scheie Syndrome, Hurler-Scheie Syndrome, Hunter syndrome, Sanfilippo syndrome, Morquio, Hyaluronidase Deficiency, Maroteaux-Lamy, Sly Syndrome, Mucolipidosis I/Sialidosis, Mucolipidosis, and Mucolipidosis, Multiple sulfatase deficiency, Niemann-Pick Disease, Neuronal Ceroid Lipofuscinoses, Pompe disease/Glycogen storage disease type II, Pycnodysostosis, Sandhoff disease, Schindler disease, Salla disease/Sialic Acid Storage Disease, Tay-Sachs/GM2 gangliosidosis and Wolman disease.

Conjugates of the invention and compositions (e.g., pharmaceutical compositions) containing conjugates of the invention can be used to treat a variety of conditions. For example, there are many conditions for which treatment therapies are known to practitioners of skill in the art in which functional agents, as disclosed herein, are employed. The invention contemplates that the conjugates of the invention (e.g., phosphorylcholine containing polymers conjugated to a variety of functional agents) and compositions containing the conjugates of the invention can be employed to treat such conditions and that such conjugates provide for an enhanced treatment therapy relative to the same functional agent not coupled to a phosphorylcholine containing polymer.

Therefore, the invention contemplates the treatment of a condition known to be treatable by a certain bioactive agent by treating the condition using the same certain bioactive agent conjugated to a phosphorylcholine containing polymer.

Another aspect of the present invention relates to methods of treating a condition responsive to a biological agent comprising administering to a subject in need thereof a therapeutically effective amount of a compound of the invention or of a pharmaceutically acceptable composition of the invention as described above. Dosage and administration are adjusted to provide sufficient levels of the bioactive agent(s) to maintain the desired effect. The appropriate dosage and/or administration protocol for any given subject may vary depending on various factors including the severity of the disease state, general health of the subject, age, weight, and gender of the subject, diet, time and frequency of administration, drug combination(s), reaction sensitivities, and tolerance/response to therapy. Therapeutically effective amounts for a given situation can be determined by routine experimentation that is within the skill and judgment of the clinician.

The pharmaceutical compositions described herein may be administered singly. Alternatively, two or more pharmaceutical compositions may be administered sequentially, or in a cocktail or combination containing two random copolymers of the present invention or one random copolymer of the present invention and another bioactive agent. Other uses of bioactive agents set forth herein may be found in standard reference texts such as the Merck Manual of Diagnosis and Therapy, Merck & Co., Inc., Whitehouse Station, N.J. and Goodman and Gilman's The Pharmacological Basis of Therapeutics, Pergamon Press, Inc., Elmsford, N.Y., (1990).

The random copolymers of the present invention are useful for treating, detecting and imaging a variety of disease states and conditions. The random copolymers can be used as a chemotherapy agent in the treatment of cancer where the initiator fragment I is not functionalized and $R^2$ includes a cancer chemotherapeutic agent $A^2$ that is loaded onto the random copolymer via click chemistry:

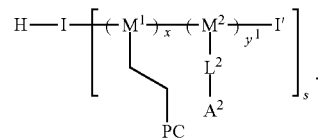

Additional cancer treatment agents using the random copolymers can include a targeting agent of an anti-angiogenic protein such as an anti-VEGF scFv fragment $A^1$ conjugated via a C-terminal cysteine to a maleimide initiator I. The random copolymer can also include a cancer chemotherapeutic agent $A^{2a}$ that is linked to the polymer backbone via a cleavable linker. Moreover, the cancer chemotherapeutic is loaded onto the random copolymer via click chemistry. For example, in Ewing's sarcoma: the targeting agent can be an anti-cancer antibody fragment such as a Fab' or scFv fragment that binds to an angiogenic growth factor such as VEGF. In addition, bone targeting comonomer $A^{2b}$ can include an aspartate rich peptide or a bisphosphonate. Other comonomers $A^{2c}$ can include Vincristine, Doxorubicin, and/or cyclophosphamide attached via a cleavable linker:

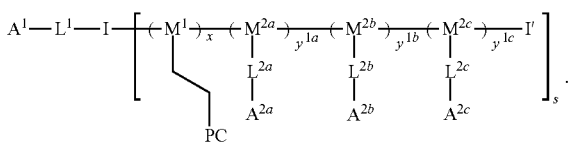

Random copolymers for more efficacious and longer residence time therapy for wet or dry macular degeneration can include an anti-inflammatory or anti-angiogenic protein such as anti-VEGF or anti-IL-6 scFv fragment $A^1$ conjugated via a C-terminal cysteine to a maleimide initiator I. The random copolymer prepared can be either a homopolymer of phosphorylcholine or a copolymer of phosphorylcholine stably attached to the polymer backbone, in combination with an anti-inflammatory small molecule or an anti-angiogenic small molecule $A^2$ linked to the polymer backbone via a cleavable linker $L^2$. Alternatively, the random copolymer can include another comonomer having a vitreous extracellular matrix (hyaluronic acid) binding moiety $A^2$ attached via a non-cleavable linker $L^2$ such as choline or a positively charged amino acid:

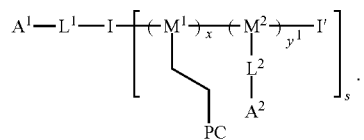

Random copolymers for real-time diagnostic estimate of tumor burden and imaging for oncology can include an anti-tumor-associated protein such as an anti-Carcino Embryonic Antigen (CEA) scFv fragment $A^1$ conjugated via a C-terminal cysteine to a maleimide initiator I. The random copolymer can include phosphorylcholine stably attached and an imaging reagent $A^{2a}$ such as a fluorescent dye (fluorescent probe detection) or gadolinium (for whole body imaging detection). Additional comonomers can be added having small molecule chemotherapy agents $A^{2b}$ to add a therapeutic element. These structures provide both therapeutic and diagnostic functions, and are commonly referred to as theranostics:

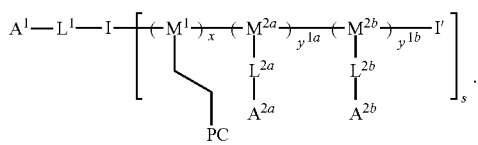

Random copolymers for use as a targeted platform for bone enzyme replacement therapies, specifically hypophosphatasia, can include recombinant alkaline phosphatase enzyme $A^1$ conjugated via aldehyde-modified initiator I through a stable linkage $L^1$. The random copolymer can include phosphorylcholine stably attached to the polymer, and a comonomer useful for targeting via a stably attached bone targeting moiety $A^2$ such as an aspartate rich peptide sequence or a bisphosphonate such that more than five targeting moieties are present ($y^1$ is greater than 5). These copolymers are useful for subcutaneous delivery:

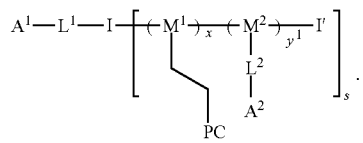

Other random copolymers are useful as a targeted platform for bone enzyme replacement therapies, specifically Morquio Syndrome (MPS type IVa). These types of random copolymers include a recombinant N-Acetylgalactosamine-6-sulfate sulfatase enzyme $A^1$ conjugated via site specific chemistry initiator I through a cleavable linker $L^1$. The random copolymer can include phosphorylcholine stably attached to the polymer, and a targeting comonomer containing a bone targeting moiety $A^2$ such as an aspartate rich peptide sequence or a bisphosphonate linked via a non-cleavable linker $L^2$, such that more than five targeting moieties are present. These copolymers are useful for subcutaneous delivery:

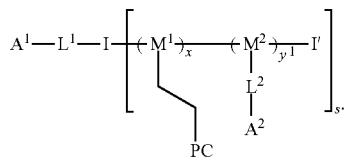

Random copolymers for targeted platforms for safer, more efficacious treatment of Rheumatoid Arthritis can include several different drugs, including an anti-TNFα biopharmaceutical such as an antibody fragment $A^1$ that is linked to the initiator I via a linker $L^2$, or an anti-VEGFR2, a small molecule $A^{2a}$, as a kinase inhibitor, and methotrexate $A^{2b}$, an antineoplastic antimetabolite with immunosuppressant properties:

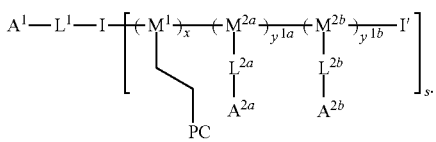

Similar random copolymers to those above can be prepared by replacing the anti-TNFα biopharmaceutical of $A^1$ with a small protein dual domain inhibitor such as an avimer or a scFv dimer that inhibits two proteins, for example TNFα and also VEGF, but without the small molecule inhibitor. In addition, the methotrexate $A^2$ can be substituted for cyclophosphamide:

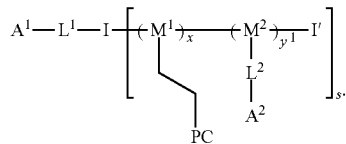

Finally, a random copolymer for targeted and protected RNAi can be prepared without a functionalized initiator I. The random copolymer can include phosphorylcholine stably attached to the polymer, and a comonomer having an siRNA $A^{2a}$ linked to the polymer via a cleavable bond $L^{2a}$, and another comonomer having a cell- or tissue-targeting group $A^{2b}$ attached via a non-cleavable linker $L^{2b}$. The siRNA containing comonomer can be prepared using a monomer having a linking group suitable for click chemistry wherein the siRNA is linked to the linking group following polymerization. The comonomer having the targeting moiety can either already contain the targeting moiety, or link to the targeting moiety via a comonomer having a linking group suitable for click chemistry via a different chemistry than for attachment of the siRNA. The cleavable linker is preferably a pH sensitive linker. The random copolymer can be prepared with a target stoichiometry of approximately five oligonucleotide moieties per drug $A^{2c}$ and five targeting moieties per drug (such that the ratio of $y^{1a}:y^{1b}:y^{1c}$ is about 5:5:1). Moreover, the phosphorylcholine polymer backbone can be optimized not for half-life, but to protect the siRNA in its journey from injection site to the targeted tissues. The siRNA can be replaced with microRNA:

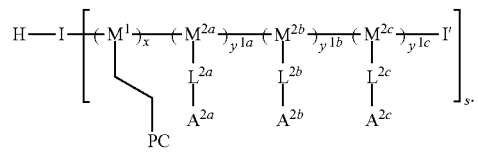

In addition, the initiator I can optionally be linked to a bioactive moiety $A^1$ such as an antibody fragment for targeting and therapy:

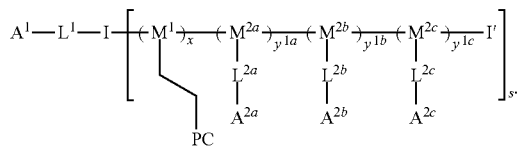

In some other embodiments, the engineering of novel multifunctional therapeutic systems can combine phosphorylcholine polymers with drug or gene targeting agent with imaging and/or sensing capabilities. Systems can have at least 3 components: (1) a targeting moiety or molecular signatures that can target delivery to specific sites, (2) the appropriate imaging agent/probe/tags for visualization or monitoring of the systems, and (3) a therapeutic agent to effectively treat a particular disease or disorder.

The following are examples of multifunctional systems that contain targeting, imaging, and drug/gene moieties. This list is not intended to be exclusive of a phosphorylcholine containing polymer system. Targeted systems that can be activated by internal processes such as pH, enzyme cleavage or external stimuli such as near IR light, ultrasound, heat, or magnetic field for therapeutic delivery and imaging are also suitable. First, our approach conceptually can be combined with all of the below:

- Synthetic biodegradable polymer-based nanoparticles encapsulating a therapeutic gene, a gadolinium contrast agent for MRI analysis, and functionalized with antibodies to target specific disease sites.
- Liposomes encapsulating small or large drug molecules, labeled with [18]Fluorine for PET analysis, and functionalized with antibodies to target specific disease sites.
- Polyplexes containing a siRNA molecule, an iron-oxide contrast agent for MRI analysis, and modified with cell binding ligands and cell-penetrating peptides for targeted cellular and intracellular delivery respectively.
- Fluorescent quantum dots intercalated with a drug molecule for optical imaging and sensing of the delivery and functionalized with an RNA aptamer to target specific diseases.
- Inorganic or organic nanoparticles containing an antisense oligonucleotide for gene therapy, a gadolinium contrast agent for MRI analysis, a fluorophore for optical imaging, and surface modified to target specific diseases.
- pH sensitive polymeric nanocomposites with a drug molecule that is released as a function of pH, an iron oxide contrast agent for MRI imaging, CdTe quantum dots for optical imaging, and functionalized with antibodies to target specific diseases.
- Nanoparticle-DNA aptamer conjugates containing a drug and a radiotracer such as $^{111}$In for SPECT imaging and functionalized with disease-specific membrane antibodies.

Second, the polymers of the present invention can be specifically combined with the above:

- Phosphorylcholine polymer-based construct containing a therapeutic gene (bioactive 1), a gadolinium contrast agent for MRI analysis (functional 1), and a small protein (such as an antibody fragment) to target specific disease sites.
- Imaging agent [18]Fluorine for PET analysis, and functionalized with small protein (such as an antibody fragment) to target specific disease sites.
- Phosphorylcholine polymers containing one or more siRNA molecules, an iron-oxide contrast agent for MRI analysis, and modified with cell binding ligands and cell-penetrating peptides for targeted cellular and intracellular delivery respectively.
- Phosphorylcholine polymers containing fluorescent quantum dots (functional agent) intercalated with a drug molecule (functional agent) for optical imaging and sensing of the delivery and functionalized with an RNA aptamer or a small protein (such as an antibody fragment or scaffold derived protein) to target specific diseases.
- Phosphorylcholine containing polymers containing an antisense oligonucleotide for gene therapy, a gadolinium contrast agent for MRI analysis, a fluorophore for optical imaging, and an additional functional agent for targeting specific diseases such as folate for tumor or choline for electrostatic interactions for targeting extracellular matrix.
- pH sensitive phosphorylcholine polymer with a drug molecule that is released as a function of pH, an iron oxide contrast agent for MRI imaging, CdTe quantum dots for optical imaging, and functionalized with antibodies or other protein or aptamer to target and treat specific diseases.
- Phosphorylcholine polymer with aptamer functional agent conjugates containing a drug and a radiotracer such as $^{111}$In for SPECT imaging and further functionalized with disease-specific membrane antibodies.

VII. Examples

Example 1

Preparation of Camptothecin PC-Copolymer

Synthesis of 2-(2-Azidoethoxy)ethanol

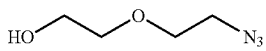

A solution of 10.0 grams of 2-(2-chloroethoxy)ethanol in 50 mL of deionized water was treated with 10.4 grams (2 eq) of sodium azide, and the reaction mixture was heated at 80° C. for 48 hours. The solution was cooled to room temperature, saturated with sodium chloride and extracted with 3×50 mL of ether. The combined organics were dried over anhydrous sodium sulfate, filtered and concentrated to give 7.25 grams (69%) of the desired product as a clear, colorless oil. $^1$H NMR (400 MHz, CDCl$_3$): δ=2.05 (t, J=6.4 Hz, 1H, OH), 3.42 (t, J=5 Hz, 2H), 3.63 (dd, J=4.4, 5.6 Hz), 3.71 (dd, J=4.4, 4.8 Hz, 2H), 3.77 (dt, J=4.4, 6 Hz, 2H).

Synthesis of 5-[2-(2-Azidoethoxy)ethoxy]-4-oxopentanoic acid

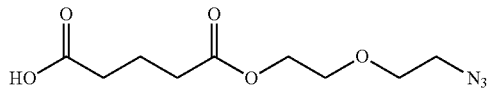 [SMILES: [N-]=[N+]=NCCOCCOC(=O)CCCC(=O)O]

A solution of 3.0 grams of 2-(2-azidoethoxy)ethanol in 50 mL of dichloromethane was treated with 280 mg of 4-(dimethylamino)pyridine and 64 mL (2 eq) of triethylamine, and the solution was cooled with an ice bath. A solution of 2.61 grams (1.0 eq) of glutaric anhydride in 5 mL of dichloromethane was then added dropwise over a few minutes. The reaction was stirred, then heated at gentle reflux overnight. The reaction was cooled to room temperature, washed with 2×25 mL of 1N HCl and 25 mL of H$_2$O, then dried over sodium sulfate. Filtration and concentration gave 4.66 grams (83%) of the desired product as a clear, colorless oil. $^1$H NMR (400 MHz, CDCl$_3$): δ=1.97 (quintet, J=7.2 Hz, 2H), 2.45 (t, J=7.2 Hz, 4H), 3.39 (t, J=4.8 Hz, 2H), 3.66-3.72 (m, 4H), 4.26 (app t, J=4.6 Hz, 2H).

Synthesis of Camptothecin azide Conjugate

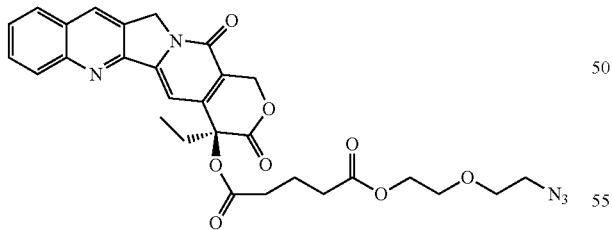

A solution of 70 mg of 5-[2-(2-azidoethoxy)ethoxy]-4-oxopentanoic acid in 10 mL of dichloromethane was cooled in an ice-water bath, and treated with 55 mg of EDC, followed by 35 mg of DMAP and 50 mg of camptothecin. The reaction was then allowed to warm to room temperature and stirred overnight as the solution slowly became homogeneous. The reaction mixture was then concentrated and applied to a silica gel column, which was eluted first with 1-2% methanol in dichloromethane. The appropriate fractions were then concentrated to give the desired conjugate as a yellow solid. $^1$H NMR (400 MHz, CDCl$_3$): δ=0.98 (t, J=7.6H), 1.98 (quintet, J=7.2 Hz, 2H), 2.13-2.32 (complex m, 2H), 2.45 (t, J=7.6 Hz, 2H), 2.51-2.65 (complex m, 2H), 3.35 (t, J=5 Hz, 2H), 3.63-3.68 (m, 4H), 4.21-4.25 (m, 2H), 5.30 (br s, 2H), 5.41 (d, J=17.2 Hz, 1H), 5.68 (d, J=17.2 Hz, 1H), 7.21 (s, 1H), 7.68 (t, J=6.8 Hz, 1H), 7.84 (app t, J=8.4 Hz, 1H), 7.95 (d, J=8 Hz, 1H), 8.23 (d, J=8 Hz, 1H), 8.40 (s, 1H).

Synthesis of Copolymer of Methacryloyloxyethyl Phosphoryl Choline and Trimethylsilyl (TMS)-Protected Propargyl Methacrylate Ethyl α-bromoisobutyrate (18.84 mg, 0.096 mmol), bipyridine (30.1 mg, 0.192 mmol) and 450 mg of DMSO were initially loaded into a Schlenk tube. The mixture was carefully degassed and the tube filled with nitrogen. CuBr was then added to the tube under inert conditions (13.8 mg, 0.096 mmol). The reaction mixture was sealed and cooled at −78 C. A mixture of trimethylsilyl (TMS)-protected propargyl methacrylate (66 mg, 0.336 mmol) and methacryloyloxyethyl phosphoryl choline (0.9, 3.04 mmol) were dissolved in 4 mL of degassed 200 proof ethanol. The solution was added drop wise under inert conditions to the cooled reaction vessel. The mixture was thoroughly degassed under vacuum for 15 min at 0° C. and filled with inert gas. Polymerization was allowed to proceed for 15 hours.

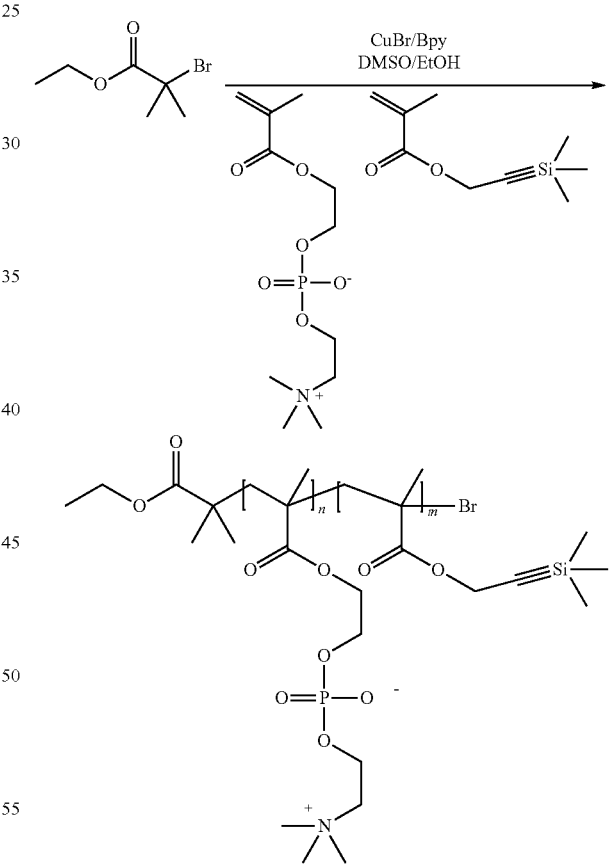

After 15 hours, the reaction mixture was found to be very homogeneous with no apparent crosslinking. The reaction was quenched by exposure to air and the mixture turned from dark brown to green.

GPC analysis of a crude sample before purification performed on a Shodex column (OH806) calibrated with polyethylene oxide standards indicated the formation of a polymer as a single peak of narrow distribution (molecular weight at peak Mp was found to be 13200 g/mol). Analysis by light scattering showed a Mn of 22900 g/mol, Mp of 25000 g/mol and PDi of 1.14. The crude reaction was passed through silica gel, concentrated and precipitated carefully into diethyl ether. The solid was isolated by filtration and washed several times with diethyl ether. Copolymer was dried inside an oven at 50 C overnight, yielding 0.9 g of copolymer.

Analysis by $^1$H NMR spectroscopy showed no TMS group. As a precautionary step, 0.5 g of the copolymer was further treated by 100 mg of tetrabutyl ammonium fluoride trihydate and purified by precipitation.

Grafting of camptothecin azide conjugate onto the alkyne-functionalized copolymer. CuBr (13 mg) was loaded inside a degassed Schlenk tube followed by the addition of 15 mg of N,N,N',N'',N''-pentamethyl diethylenetriamine. 240 mg of copolymer was dissolved into 2 g of 200 proof degassed ethanol and 50 mg of camptothecin azide conjugate (CPT-L-N3) were dissolved into 1.5 g of DMF. The solution of CPT-L-N3 was added dropwise under inert conditions to the Schlenk tube while stirring, followed by the addition of the solution of alkyne-functionalized copolymer. The mixture was degassed by three cycles of vacuum-nitrogen and was allowed to react at room temperature for 3 hours.

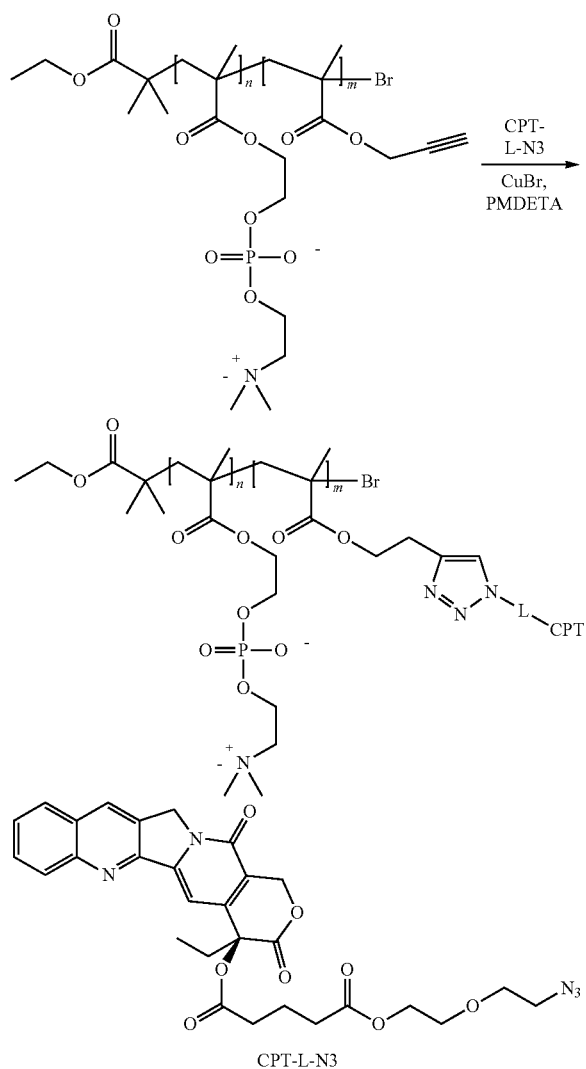

CPT-L-N3

After 3 hours, an aliquot was taken from the crude mixture and analyzed by GPC at 370 nm which showed the disappearance of the free camptothecin peak and a high molecular weight peak which corresponded to the camptothecin copolymer conjugate.

The reaction mixture was exposed to air, concentrated to half its volume, passed through silica gel to remove the copper catalyst and then precipitated carefully into diethyl ether. The polymer was washed with an excess of diethyl ether. The solid was isolated by filtration and washed several times with diethyl ether. The polymer was dried in an oven at 50 C overnight and was isolated as a light-brown powder. $^1$H NMR spectroscopy analysis performed on the camptothecin grafted copolymers (CD$_3$OD) showed weak and broad aromatic signals in the 7-9 ppm area, characteristic of protons from the incorporated camptothecin.

Example 2

Camptothecin Release Study from Camptothecin Grafted Copolymer

Samples of camptothecin grafted copolymer were prepared at approximately 10 mg/mL in Tris Buffer, pH=8.0. Liver esterase from rabbit liver (Sigma-Aldrich E0887-IKU, Lot #061K74451) was added to the sample and the sample was incubated at 37° C. for up to 65 hours.

GPC analysis of the samples was made using an HPLC system consisting of a Waters Alliance 2995 with Waters 2410 Refractive Index Detector, Waters 2996 Photodiode Array Detector, and a Shodex Protein KW-803 column. The mobile phase used for the elution was phosphate buffered saline containing 10% absolute ethanol. The flow rate was set to 1 mL/min and the presence of camptothecin monitored at 370 nm. Ten microliter injections of the samples were made at each time point.

| Time (h) | mg/mL Camptothecin Released |
|---|---|
| 0 | 0.059 |
| 1 | 0.079 |
| 2 | 0.132 |
| 3 | 0.130 |
| 4 | 0.128 |
| 17 | 0.208 |
| 26 | 0.251 |
| 41 | 0.335 |
| 65 | 0.427 |

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:
1. A random copolymer of Formula I:
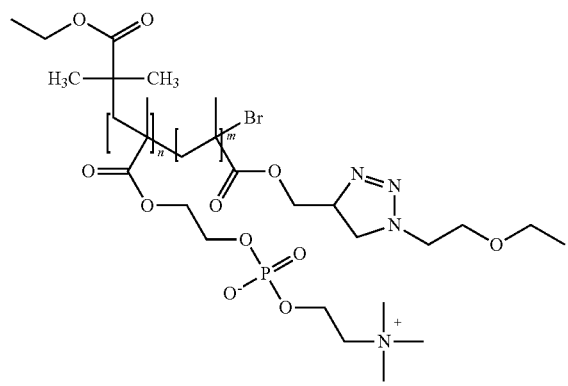
wherein n and m are each independently from 1-1000.
2. A method of treating cancer, comprising administering an ameliorative amount of the random copolymer of claim 1 to a subject in need thereof, wherein the cancer is colon cancer, lung cancer, breast cancer, stomach cancer, ovarian cancer, or malignant melanoma.
* * * * *